(12) United States Patent
Ross et al.

(10) Patent No.: US 7,265,150 B1
(45) Date of Patent: Sep. 4, 2007

(54) CARBOXYLIC ACIDS AND CARBOXYLIC ACID ISOSTERES OF N-HETEROCYCLIC COMPOUNDS FOR VISION AND MEMORY DISORDERS

(75) Inventors: Douglas T. Ross, North Wales, PA (US); Hansjörg Sauer, Silver Spring, MD (US); Gregory S. Hamilton, Catonsville, MD (US); Joseph P. Steiner, Finksburg, MD (US)

(73) Assignee: GPI NIL Holdings Inc., Wilmington, DE (US)

( * ) Notice: Subject to any disclaimer, the term of this patent is extended or adjusted under 35 U.S.C. 154(b) by 0 days.

(21) Appl. No.: 09/134,472

(22) Filed: Aug. 14, 1998

(51) Int. Cl.
*A01N 43/36* (2006.01)
*A61K 31/40* (2006.01)
*C07D 221/02* (2006.01)

(52) U.S. Cl. ............... 514/423; 548/543; 548/533; 548/311.1; 548/265.1; 548/492; 546/183; 546/189; 546/286

(58) Field of Classification Search ......... 514/423; 548/543, 533, 311.1, 356.1, 492; 546/183, 546/139, 286
See application file for complete search history.

(56) References Cited

U.S. PATENT DOCUMENTS

| | | | |
|---|---|---|---|
| 4,839,342 A | 6/1989 | Kaswan | 514/11 |
| 5,011,844 A | 4/1991 | Fehr | 514/291 |
| 5,189,042 A | 2/1993 | Goulet et al. | 514/291 |
| 5,192,773 A | 3/1993 | Armistead et al. | 514/315 |
| 5,194,434 A | 3/1993 | Chiou et al. | 514/227.2 |
| 5,198,454 A | 3/1993 | Chiou et al. | 514/369 |
| 5,244,902 A | 9/1993 | Sharpe et al. | 514/278 |
| 5,252,319 A | 10/1993 | Babcock et al. | 424/78.04 |
| 5,258,389 A | 11/1993 | Goulet et al. | 514/291 |
| 5,284,826 A | 2/1994 | Eberle | 514/11 |
| 5,368,865 A | 11/1994 | Asakura et al. | 424/489 |
| 5,387,589 A | 2/1995 | Kulkarni | 514/291 |
| 5,441,937 A | 8/1995 | Wallace et al. | 514/21 |
| 5,441,977 A | 8/1995 | Russo et al. | 514/411 |
| 5,457,111 A | 10/1995 | Luly et al. | 514/291 |
| 5,468,752 A | 11/1995 | Freeman | 514/272 |
| 5,514,686 A | 5/1996 | Mochizuki et al. | 514/297 |
| 5,527,533 A | 6/1996 | Tso et al. | 424/422 |
| 5,532,248 A | 7/1996 | Goulet et al. | 514/291 |
| 5,620,921 A | 4/1997 | Sullivan | 514/178 |
| 5,632,984 A | 5/1997 | Wong et al. | 424/85.4 |
| 5,641,749 A | 6/1997 | Louis | 514/12 |
| 5,641,750 A | 6/1997 | Louis | 514/12 |
| 5,667,968 A | 9/1997 | LaVail et al. | 514/12 |
| 5,688,765 A | 11/1997 | Sullivan | 514/12 |
| 5,693,645 A | 12/1997 | Sharpe et al. | 514/278 |
| 5,700,909 A | 12/1997 | O'Brien | 530/326 |
| 5,736,516 A | 4/1998 | Louis | 514/12 |
| 5,935,989 A * | 8/1999 | Hamilton et al. | 514/423 |
| 6,140,357 A * | 10/2000 | Hamilton et al. | 514/423 |

FOREIGN PATENT DOCUMENTS

WO    WO9827975    7/1998

OTHER PUBLICATIONS

Merriam-Webster's Collegiate Dictionary, Deluxe Edition, published by Merriam-Webster (1998), Inc., Springfield, Mass., p. 53.*
Wermuth et al. Pure & Appl. Chem. (1998), vol. 70, pp. 1129-1143.*
Teri et al., "Imipramine in the Treatment of Depressed Alzheimer's Patients: Impact on Cognition", Journal of Gerontology, Psychological Sciences, vol. 46, pp. 372-377 (1991).

* cited by examiner

*Primary Examiner*—Patrick Lewis
(74) *Attorney, Agent, or Firm*—Foley & Lardner LLP

(57) ABSTRACT

This invention relates to novel compositions and uses of N-heterocyclic carboxylic acids and carboxylic acid isosteres for treating a vision disorder, improving vision, treating memory impairment or enhancing memory performance in an animal.

25 Claims, 9 Drawing Sheets

Figure 1

GPI 1046 protects ganglion cells against degeneration due to 1 hour of retinal ischemia
Florogold labelled retinal ganglion cells in wholemount, 28 days after ischmic episode

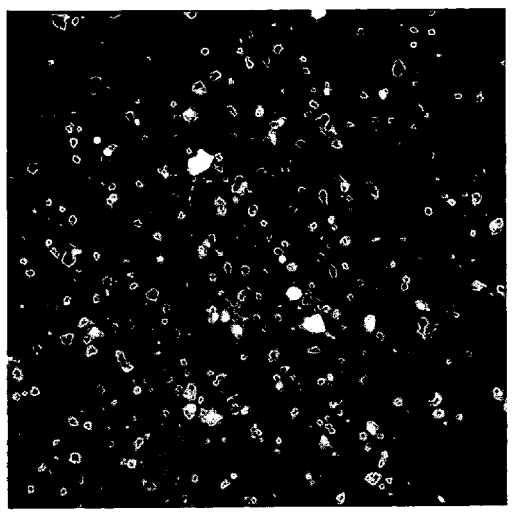

A. Labelled retinal ganglion cells in the
Normal central retina

B. 1 hour of retinal ischemia produces
extensive loss of ganglion cells

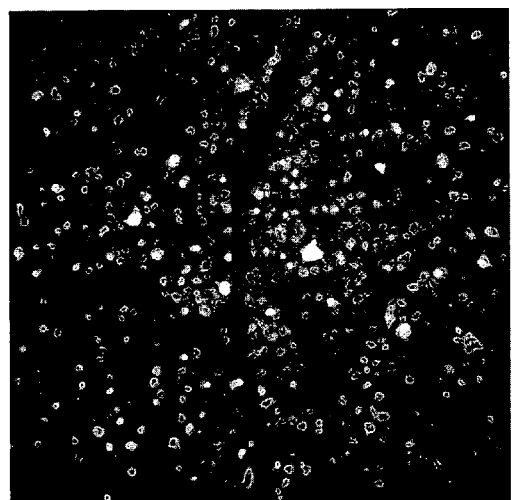

B. Administration of GPI 1046 1 hour before retinal ischemia
and for 4 days subsequently produces significant protection of vulnerable retinal ganglion cells GPI 1046 Protects retinal ganglion cell axons and prevents myelin degeneration in the optic nerve induced by 1 hour of complete retinal ischemia, toluidine blue stained optic nerve cross sections, 630X A. Normal optic nerve B. Vehicle treated optic nerve 28 days after 1 hour complete retinal ischemia C. GPI 1046 treated optic nerve 28 days after 1 hour complete retinal ischemia Figure 3
GPI 1046 administration for 28 days provides only moderate protection of axotomized retinal ganglion cells
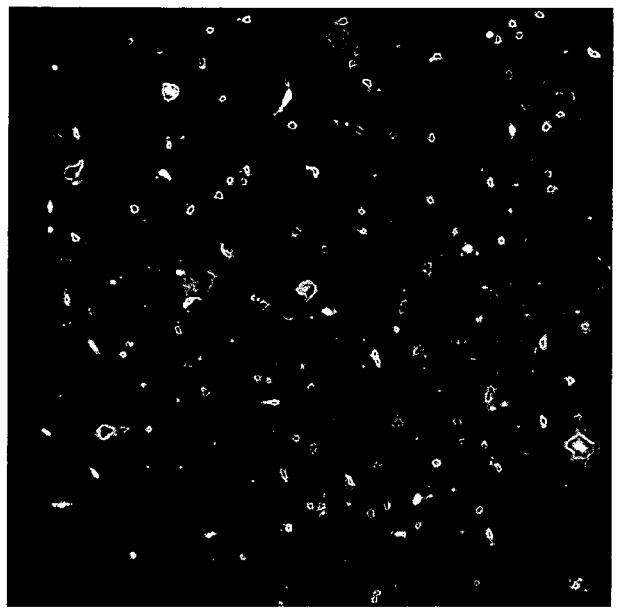
Florogold labelled RGCs 90 days following transection,
Treatment with vehicle alone for 1st 28 days
Florogold labelled RGCs 90 days following transection,
Treatment with GPI 1046 for 1st 28 days
Treatment with vehicle alone for 1st 28 days
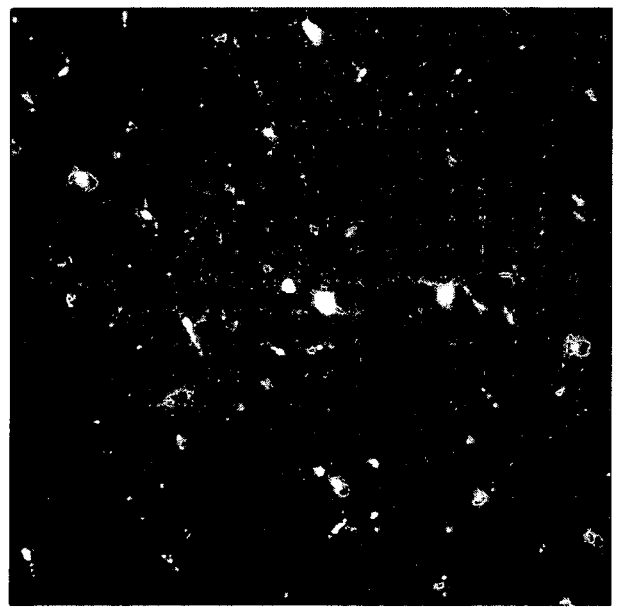

Figure 4
GPI 1046 prevents axonal degeneration in the proximal stump of the optic nerve
RT97 neurofilament immunohistochemistry,
optic nerve cross sections, 90 days after complete transection
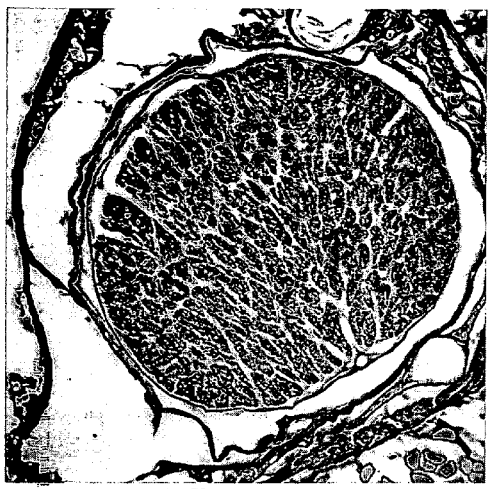
A. Sham
B. Optic nerve transection (ONT) 90 days survival
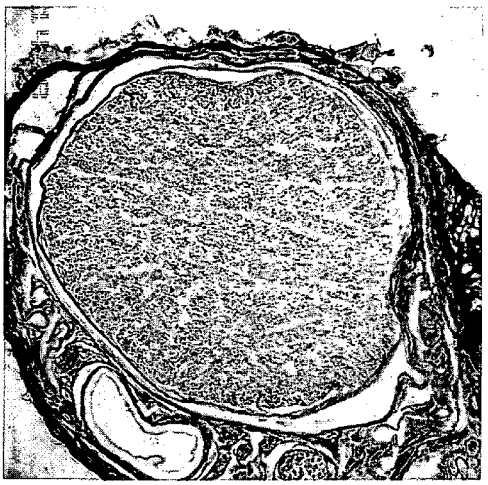
C. optic nerve 90 days after transection,
GPI 1046 treatment days 1-28
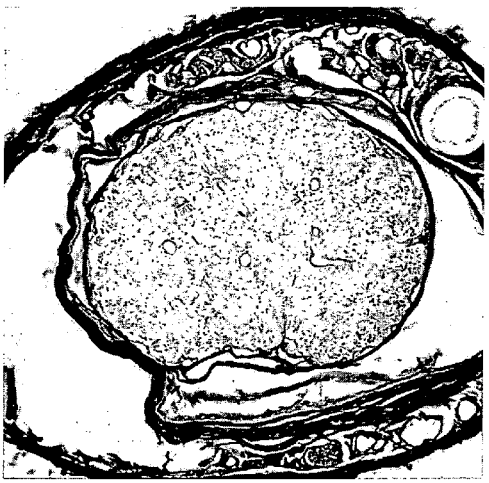
D. optic nerve 90 days after transection,
GPI 1046 treatment days 1-14

Figure 5
GPI 1046 administration for 28 days provides only moderate protection of axotomized retinal ganglion cells
Florogold labelled retinal ganglion cells 90 days following transection

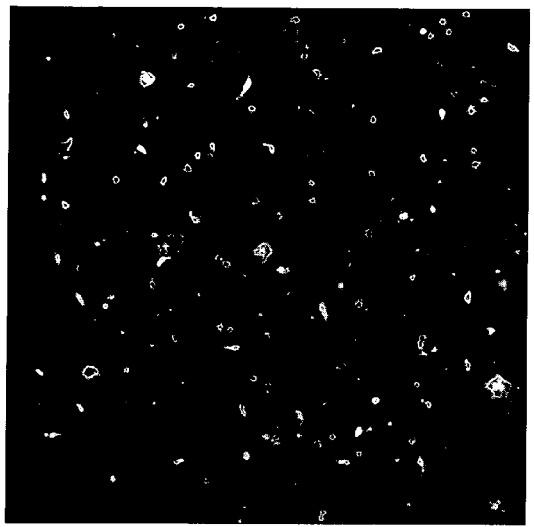 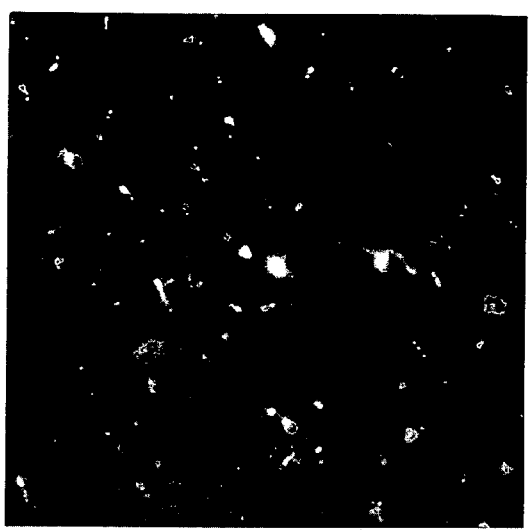

vehicle administered for 1st 28 days GPI 1046 administered for 1st 28 days

GPI 1046 administration for 28 days preserves optic nerve axons of surviving retinal ganglion cells
RT 97 neurofilament immunohistochemistry 90days after transection

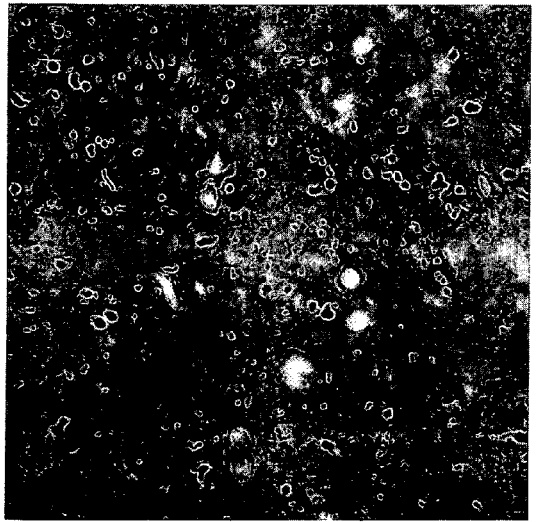 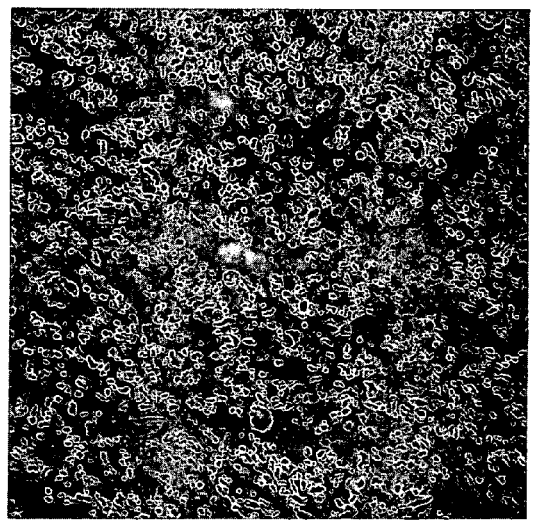

vehicle administered for 1st 28 days GPI 1046 administered for 1st 28 days

Figure 6
Preservation of myelin in the proximal stump of the optic nerve 90 days after transection
14 vs 28 days treatment with GPI 1046 10mg/kg s.c.
Normal( sham) Optic nerve
90 days after optic nerve transection, vehicle treated
90 days after optic nerve transection, 14 days GPI 1046
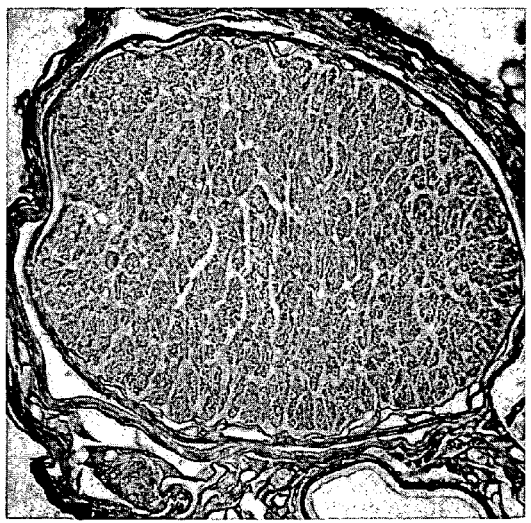
90 days after optic nerve transection, 28 days GPI 1046
myelin basic protein immunohistochemistry (SMI-94), 20X FKBP-12 immunohistochemistry labels oligodendroglia and axons in the normal optic nerve

Figure 8

**GPI 1046 treatment prevents myelin degeneration
in the distal stump of the optic nerve
Myelin basic protein immunohistochemistry 90 days after transection**

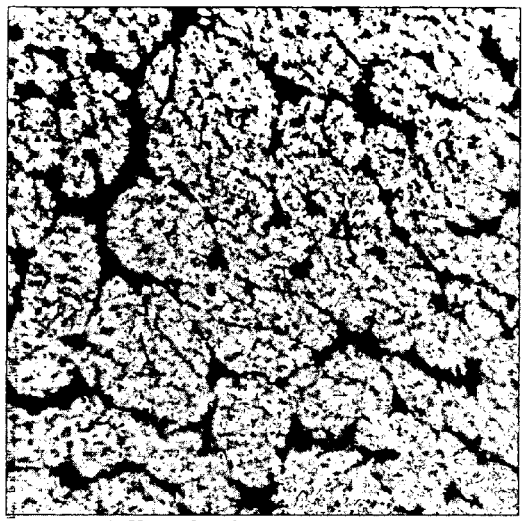

A. Normal optic nerve

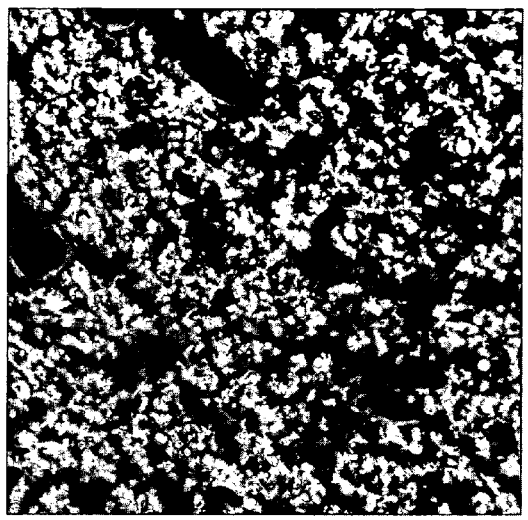

B. Distal optic nerve stump
90 days after complete transection

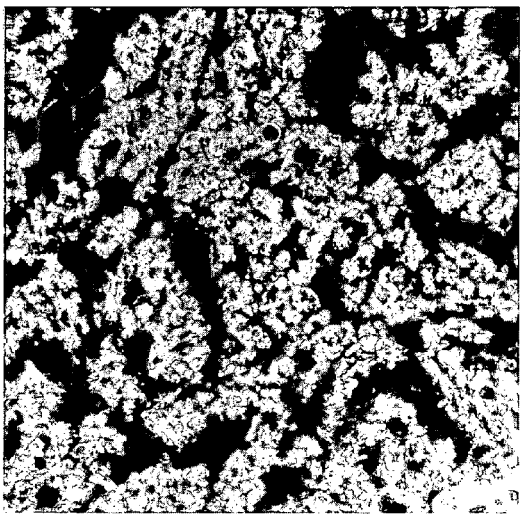

C. Distal optic nerve stump
90 days after complete transection
GPI 1046 administered 1-14 days
after transection

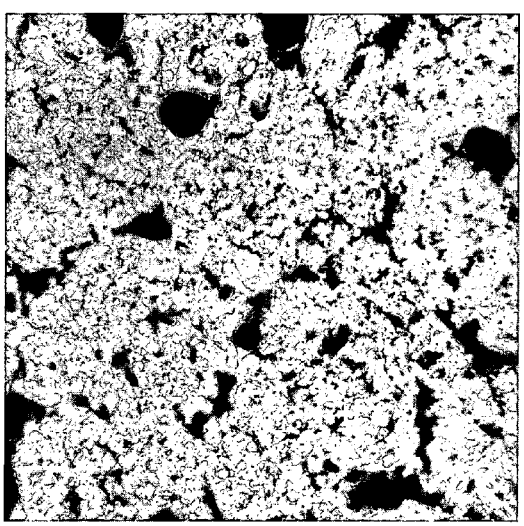

D. Distal optic nerve stump
90 days after complete transection
GPI 1046 administered 1-28 days
after transection Figure 9
GPI 1046 decreases neovascularization and prevents neuronal loss in the inner retinal in the Streptozotocin model of diabetic retinopathy A. Normal
retina
Cross section
Cresyl violet Outer Nuclear
layer (ONL)

Inner Nuclear
layer(INL)

Ganglion cell
layer (GCL)

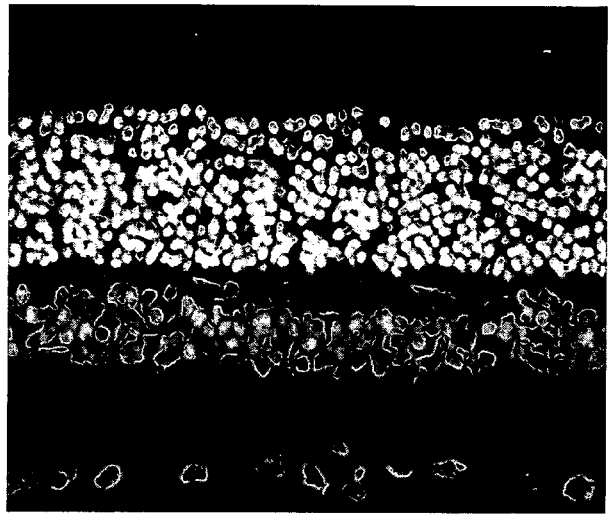

B. retina from
Streptozotocin
/vehicle case

ONL

INL

GCL

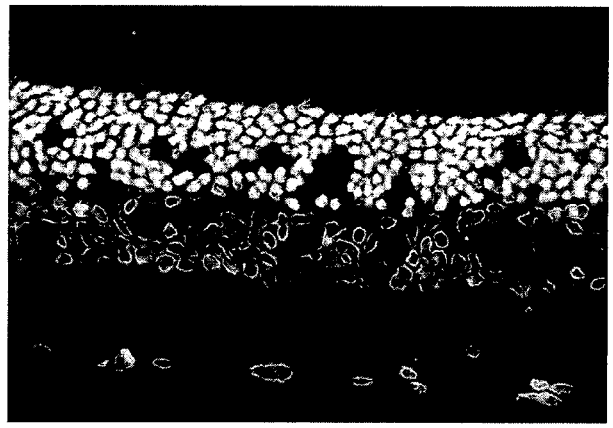

C. Retina from
Streptozotocin
/GPI 1046 case

ONL

INL

GCL

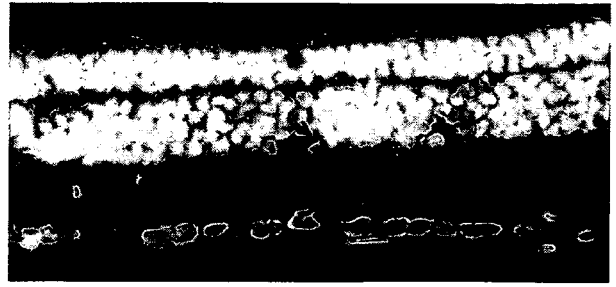

CARBOXYLIC ACIDS AND CARBOXYLIC ACID ISOSTERES OF N-HETEROCYCLIC COMPOUNDS FOR VISION AND MEMORY DISORDERS

BACKGROUND OF THE INVENTION

1. Field of Invention

This invention relates to pharmaceutical compositions and methods for treating vision loss, preventing vision degeneration, and promoting vision regeneration ("neopsis") using low molecular weight, small molecule derivatives.

2. Description of Related Art

The visual system is composed of the eyes, ocular adnexa and the visual pathways. Dysfunction of the visual system may lead to permanent or temporary visual impairment, i.e. a deviation from normal in one or more functions of the eye. Visual impairment manifests itself in various ways and includes a broad range of visual dysfunctions and disturbances. Without limitation, these dysfunctions and disturbances include partial or total loss of vision, the need for correction of visual acuity for objects near and far, loss of visual field, impaired ocular motility without diplopia (double vision), impaired or skewed color perception, limited adaptation to light and dark, diminished accommodation, metamorphopsic distortion, impaired binocular vision, paresis of accommodation, iridoplegia, entropion, ectropion, epiphora, lagophthalmos, and scarring. See *Physicians' Desk Reference (PDR) for Ophthalmology*, 16th Edition, 6:47 (1988). The visual system may be adversely affected by various ophthalmologic disorders, diseases, injuries, and complications, including, without limitation, genetic disorders; [non-genetic disorders;] disorders associated with aging or degenerative diseases; disorders correlating to physical injury to the eye, head, or other parts of the body resulting from external forces; disorders resulting from environmental factors; disorders resulting from a broad range of diseases; and combinations of any of the above.

The visual system is a complex system composed of numerous components. Visual impairment can involve the entire visual system, any one component, or any combination of components, depending upon the precise nature of the circumstances. The eye is composed of a lens, which is suspended in the zonules of Zinn and is focused by the ciliary body. The ciliary body also secretes aqueous humor, which fills the posterior chamber, passes through the pupil into the anterior chamber, then drains primarily via the canal of Schlemm. The iris regulates the quantity of light entering the eye by adjusting the size of its central opening, the pupil. A visual image is focused onto the retina, the fovea centralis being the retinal area of sharpest visual acuity. The conjunctiva is the mucus membrane which lines the eyelids and the eyeball, and ends abruptly at the limbus conjunctivae, the edge of the conjunctiva overlapping the cornea. The cornea is the clear, transparent anterior portion of the fibrous coat of the eye; it is important in light refraction and is covered with an epithelium that differs in many respects from the conjunctival epithelium.

The retina is the innermost, light sensitive portion of the eye, containing two types of photoreceptors, cones, which are responsible for color vision in brighter light, and rods, which are essential for vision in dim light but do not perceive colors. After light passes through the cornea, lens system, and the vitreous humor, it enters the retina from the inside; that is, it passes through the ganglion cells and nerve fibers, the inner and outer plexiform layers, the inner and outer nuclear layers, and the internal and external limiting membranes before it finally reaches the layer of photoreceptors located near the outside of the retina, just inside the outermost pigment epithelium layer. The cells of the pigment epithelium layer act as an anatomical barrier to liquids and substances located outside of the eye, forming the "blood-retina" barrier, and provide nourishment, oxygen, a source of functionally useful substances like vitamin A, and phagocytosis of decomposition products to photoreceptor cells. There is no anatomical connection between the pigment epithelium and the photoreceptor layer, permitting separation of the layers in some pathological situations.

When rods or cones are excited by light, signals are transmitted through successive neurons in the retina itself, into the optic nerve fibers, and ultimately to the cerebral cortex. Both rods and cones contain molecules that decompose on exposure to light and, in the process, excite the nerve fibers leading from the eye. The molecule in rods is rhodopsin. The three light-sensitive molecules in cones, collectively called iodopsin, have compositions only slightly different from that of rhodopsin and are maximally excited by red, blue, or green light, respectively.

Neither rods nor cones generate action potentials. Rather, the light-induced membrane hyperpolarization generated in the outer, photosensitive segment of a rod or cone cell is transmitted from the outer segment through the inner segment to the synaptic body by direct conduction of the electrical voltage itself, a process called electrotonic conduction. At the synaptic body, the membrane potential controls the release of an unknown transmitter molecule. In low light, rod and cone cell membranes are depolarized and the rate of transmitter release is greatest. Light-induced hyperpolarization causes a marked decrease in the release of transmitter molecules.

The transmitters released by rod and cone cells induce signals in the bipolar neurons and horizontal cells. The signals in both these cells are also transmitted by electrotonic conduction and not by action potential.

The rod bipolar neurons connect with as many as 50 rod cells, while the dwarf and diffuse bipolar cells connect with one or several cone cells. A depolarizing bipolar cell is stimulated when its connecting rods or cones are exposed to light. The release of transmitter molecules inhibits the depolarizing bipolar cell. Therefore, in the dark, when the rods and cones are secreting large quantities of transmitter molecules, the depolarizing bipolar cells are inhibited. In the light, the decrease in release of transmitter molecules from the rods and cones reduces the inhibition of the bipolar cell, allowing it to become excited. In this manner, both positive and negative signals can be transmitted through different bipolar cells from the rods and cones to the amacrine and ganglion cells.

As their name suggests, horizontal cells project horizontally in the retina, where they may synapse with rods, cones, other horizontal cells, or a combination of cells types. The function of horizontal cells is unclear, although some mechanism in the convergence of photoreceptor signaling has been postulated.

All types of bipolar cells connect with ganglion cells, which are of two primary types. A-type ganglion cells predominately connect with rod bipolar cells, while B-type ganglion cells predominately connect with dwarf and diffuse bipolar cells. It appears that A-type ganglion cells are sensitive to contrast, light intensity, and perception of movement, while B-type ganglion cells appear more concerned with color vision and visual acuity.

Like horizontal cells, the Amacrine cells horizontally synapse with several to many other cells, in this case bipolar cells, ganglion cells, and other Amacrine cells. The function of Amacrine cells is also unclear.

The axons of ganglion cells carry signals into the nerve fiber layer of the eye, where the axons converge into fibers which further converge at the optic disc, where they exit the eye as the optic nerve. The ganglion cells transmit their signals through the optic nerve fibers to the brain in the form of action potentials. These cells, even when unstimulated, transmit continuous nerve impulses at an average, baseline rate of about 5 per second. The visual signal is superimposed onto this baseline level of ganglion cell stimulation. It can be either an excitatory signal, with the number of impulses increasing above the baseline rate, or an inhibitory signal, with the number of nerve impulses decreasing below the baseline rate.

As part of the central nervous system, the eye is in some ways an extension of the brain; as such, it has a limited capacity for regeneration. This limited regeneration capacity further complicates the challenging task of improving vision, resolving dysfunction of the visual system, and/or treating or preventing ophthalmologic disorders. Many disorders of the eye, such as retinal photic injury, retinal ischemia-induced eye injury, age-related macular degeneration, free radical-induced eye diseases, as well as numerous other disorders, are considered to be entirely untreatable. Other ophthalmologic disorders, e.g., disorders causing permanent visual impairment, are corrected only by the use of ophthalmic devices and/or surgery, with varying degrees of success.

The immunosuppressant drugs FK506, rapamycin, and cyclosporin are well known as potent T-cell specific immunosuppressants, and are effective against autoimmunity, transplant or graft rejection, inflammation, allergic responses, other autoimmune or immune-mediated diseases, and infectious diseases. It has been disclosed that application of Cyclosporin, FK-506, Rapamycin, Buspirone, Spiperone, and/or their derivatives are effective in treating some ophthalmologic disorders of these types. Several ophthalmologic disorders or vision problems are known to be associated with autoimmune and immunologically-mediated activities; hence, immunomodulatory compounds are expected to demonstrate efficacy for treating those types of ophthalmologic disorders or vision problems.

The effects of FK506, Rapamycin, and related agents in the treatment of ophthalmologic diseases are disclosed in several U.S. patents (Goulet et al., U.S. Pat. No. 5,532,248; Mochizuki et al., U.S. Pat. No. 5,514,686; Luly et al., U.S. Pat. No. 5,457,111; Russo et al., U.S. Pat. No. 5,441,937; Kulkarni, U.S. Pat. No. 5,387,589; Asakura et al., U.S. Pat. No. 5,368,865; Goulet et al., U.S. Pat. No. 5,258,389; Armistead et al., U.S. Pat. No. 5,192,773; Goulet et al., U.S. Pat. No. 5,189,042; and Fehr, U.S. Pat. No. 5,011,844). These patents claim FK506 or Rapamycin related compounds and disclose the known use of FK506 or Rapamycin related compounds in the treatment of ophthalmologic disorders in association with the known immunosuppressive effects of FK506 and Rapamycin. The compounds disclosed in these patents are relatively large. Further, the cited patents relate to immunomodulatory compounds limited to treating autoimmunity or related diseases, or immunologically-mediated diseases, for which the efficacy of FK506 and Rapamycin is well known.

Other U.S. patents disclose the use of cyclosporin, Spiperone, Buspirone, their derivatives, and other immunosuppressive compounds for use in the treatment of ophthalmologic diseases (Sharpe et al., U.S. Pat. No. 5,703,088; Sharpe et al., U.S. Pat. No. 5,693,645; Sullivan, U.S. Pat. No. 5,688,765; Sullivan, U.S. Pat. No. 5,620,921; Sharpe et al., U.S. Pat. No. 5,574,041; Eberle, U.S. Pat. No. 5,284,826; Sharpe et al., U.S. Pat. No. 5,244,902; Chiou et al., U.S. Pat. Nos. 5,198,454 and 5,194,434; and Kaswan, U.S. Pat. No. 4,839,342). These patents also relate to compounds useful for treating autoimmune diseases and cite the known use of cyclosporin, Spiperone, Buspirone, their derivatives, and other immunosuppressive compounds in treating ocular inflammation and other immunologically-mediated ophthalmologic diseases.

The immunosuppressive compounds disclosed in the prior art suppress the immune system, by definition, and also exhibit other toxic side effects. Accordingly, there is a need for non-immunosuppressant, small molecule compounds, and compositions and methods for use of such compounds, that are useful in improving vision; preventing, treating, and/or repairing visual impairment or dysfunction of the visual system; and preventing, treating, and/or resolving ophthalmologic disorders.

There are also a number of patents on non-immunosuppressive compounds disclosing methods of use for permitting or promoting wound healing (whether from injury or surgery); controlling intraocular pressure (often resulting from glaucoma); controlling neurodegenerative eye disorders, including damage or injury to retinal neurons, damage or injury to retinal ganglion cells, and macular degeneration; stimulating neurite outgrowth; preventing or reducing oxidative damage caused by free radicals; and treating impaired oxygen and nutrient supply, as well as impaired waste product removal, resulting from low blood flow. These non-immunosuppressive substances fall into one of two general categories: naturally occurring molecules, such as proteins, glycoproteins, peptides, hormones, and growth factors; and synthetic molecules.

Within the group of naturally occurring non-immunosuppressive molecules, several hormones, growth factors, and signaling molecules have been patented for use as supplements to naturally occurring quantities of such molecules, as well as for targeting of specific cells where the particular molecule does not naturally occur in a mature individual. These patents generally claim methods of use for reducing or preventing the symptoms of ocular disease, or arresting or reversing vision loss.

Specifically, Louis et al., U.S. Pat. Nos. 5,736,516 and 5,641,749, disclose the use of a glial cell line derived neurotrophic factor (GDNF) to stop or reverse the degeneration of retinal neurons (i.e. photoreceptors) and retinal ganglion cells caused by glaucoma, or other degenerative or traumatic retinal diseases or injuries. O'Brien, et al., U.S. Pat. Nos. 5,714,459 and 5,700,909, disclose the use of a glycoprotein, Saposin, and its derivatives for stimulating neurite outgrowth and increasing myelination. To stop or reverse degeneration of retinal neurons, LaVail et al., U.S. Pat. No. 5,667,968, discloses the use of a variety of neurotrophic proteins, including brain-derived neurotrophic factor, ciliary neurotrophic factor, neurotrophin-3 or neurotrophin-4, acidic or basic fibroblast growth factors, interleukin, tumor necrosis factor-α, insulin-like growth factor-2 and other growth factors. Wong et al., U.S. Pat. No. 5,632,984, discloses the use of interferons, especially interferon α-2a, for treating the symptoms of macular degeneration by reducing hemorrhage and limiting neovascularization. Finally, Wallace et al., U.S. Pat. No. 5,441,937, discloses the use of a lung-derived neurotrophic factor (NTF) to maintain the functionality of ciliary ganglion and parasympathetic neuron cells.

A key characteristic of factors derived from specific cell lines is their localization to specific cell lines or tissues; systemic treatment with these molecules would run a substantial risk of unintended, and potentially dangerous, effects in cell lines where the genes encoding these molecules are inactive. Similarly, hormones and growth factors often activate a large number of genes in many cell lines; again, non-localized application of these molecules would run a substantial risk of provoking an inappropriate, and potentially dangerous, response.

Within the category of synthetic molecules, most of the patented compounds are immunosuppressive and disclose uses in treating inflammatory, autoimmune, and allergic responses, as discussed above. A few others are non-immunosuppressive and claim the ability to treat cellular degeneration, and in some cases promote cellular regeneration, most often in the context of their antioxidant properties.

Specifically, Tso et al., U.S. Pat. No. 5,527,533, discloses the use of astaxanthin, a carotenoid antioxidant, for preventing or reducing photoreceptor damage resulting from the presence of free radicals. Similarly, Babcock et al., U.S. Pat. No. 5,252,319, discloses the use of antioxidant aminosteroids for treating eye disease and injury, by increasing resistance to oxidative damage. Freeman, U.S. Pat. No. 5,468,752, discloses the use of the antiviral phosphonylmethoxyalkylcytosines to reduce abnormally increased intraocular pressure.

Hamilton and Steiner disclose in U.S. Pat. No. 5,614,547 novel pyrrolidine carboxylate compounds which bind to the immunophilin FKBP12 and stimulate nerve growth, but which lack immunosuppressive effects. Unexpectedly, it has been discovered that these non-immunosuppressant compounds promote improvements in vision and resolve ophthalmologic disorders. Yet their novel small molecule structure and non-immunosuppressive properties differentiate them from FK506 and related immunosuppressive compounds found in the prior art.

Further, these compounds may be differentiated from the non-immunosuppressive compounds used to treat vision disorders by their, novel small molecule structure and their lack of general, systemic effects. Naturally occurring hormones, growth factors, cytokines, and signaling molecules are generally multifunctional and activate many genes in diverse cell lines. The present compounds do not, thus avoiding the unexpected, and potentially dangerous, side effects of systemic use. Similarly, the present compounds also avoid the potential unexpected side effects of introducing cell line-specific molecules into other cell lines were they do not naturally occur.

SUMMARY OF THE INVENTION

The present invention relates to the surprising discovery that N-heterocyclic compounds containing a carboxylic acid or isostere thereof may be useful for treating a vision disorder, improving vision, treating memory impairment or enhancing memory performance in an animal. Accordingly, novel compositions and methods of using N-heterocyclic ring compounds containing an acidic moiety or an isostere thereof attached to the 2-carbon of the N-heterocyclic ring are provided. A preferred feature of the compounds of the present invention is that they do not exert any significant immunosuppressive activity.

Preferred embodiments of this invention include methods and compositions containing a compound having the formula (I):

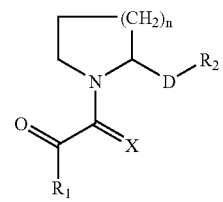

where n is 1–3;

X is either O or S;

$R_1$ is selected from the group consisting of $C_1$–$C_9$ straight or branched chain alkyl, $C_2$–$C_9$ straight or branched chain alkenyl, aryl, heteroaryl, carbocycle, or heterocycle;

D is a bond, or a $C_1$–$C_{10}$ straight or branched chain alkyl, $C_2$–$C_{10}$ alkenyl or $C_2$–$C_{10}$ alkynyl; and $R_2$ is a carboxylic acid or a carboxylic acid isostere; or a pharmaceutically acceptable salt, ester, or solvate thereof;

Preferred embodiments of this invention are where $R_2$ is a carbocycle or heterocycle containing any combination of $CH_2$, O, S, or N in any chemically stable oxidation state, where any of the atoms of said ring structure are optionally substituted in one or more positions with $R^3$.

Especially preferred embodiments of this invention are where $R_2$ is selected from the group below:

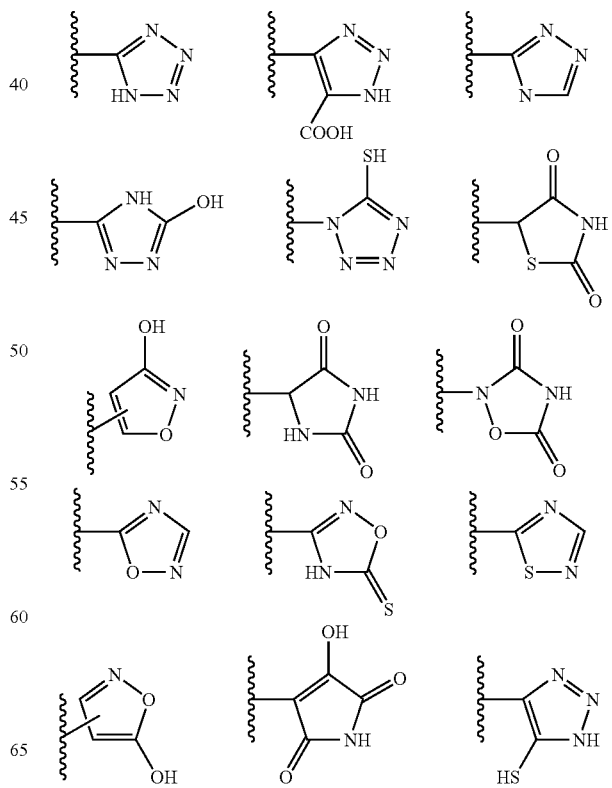

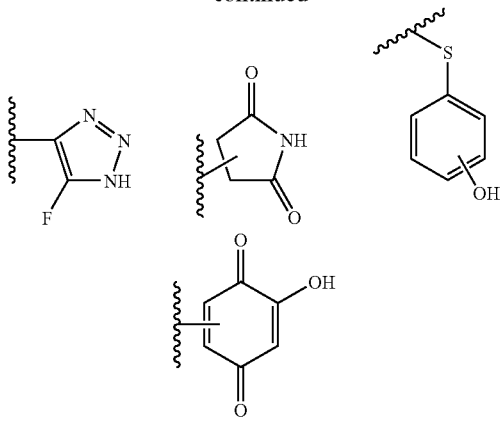

where the atoms of said ring structure may be optionally substituted at one or more positions with R³, where R³ is hydrogen, hydroxy, halo, haloalkyl, thiocarbonyl, alkoxy, alkenoxy, alkylaryloxy, aryloxy, arylalkyloxy, cyano, nitro, imino, alkylamino, aminoalkyl, sulfhydryl, thioalkyl, alkylthio, sulfonyl, $C_1$–$C_6$ straight or branched chain alkyl, $C_2$–$C_6$ straight or branched chain alkenyl or alkynyl, aryl, heteroaryl, carbocycle, heterocycle, and $CO_2R^4$ where $R^4$ is hydrogen or $C_1$–$C_9$ straight or branched chain alkyl or alkenyl.

Another preferred embodiment of this invention is where $R_2$ is selected from the group consisting of —COOH, —$SO_3H$, —$SO_2HNR^3$, —$PO_2(R^3)_2$, —CN, —$PO_3(R^3)_2$, —$OR^3$, —$SR^3$, —$NHCOR^3$, —$N(R^3)$ 2, —$CON(R^3)_2$, —$CONH(O)R^3$, —$CONHNHSO_2R^3$—$COHNSO_2R^3$, and —$CONR^3CN$.

Preferred compounds of this invention are: (2S)-1-(1,2-dioxo-3,3-dimethylpentyl)-2-hydroxymethyl pyrrolidine; (2S)-1-(1,2-dioxo-3,3-dimethylpentyl)-2-pyrrolidinetetrazole; (2S)-1-(1,2-dioxo-3,3-dimethylpentyl)-2-pyrrolidinecarbonitrile; and (2S)-1-(1,2-dioxo-3,3-dimethylpentyl)-2-aminocarbonyl piperidine, and compounds 1–136 of Tables I, II, and III.

BRIEF DESCRIPTION OF THE DRAWINGS

FIGS. 1 A, B and C show that GPI 1046 protects retinal ganglion cells against degeneration following retinal ischemia.

FIG. 3 shows that GPI 1046 provides moderate protection against retinal ganglion cell death after optic nerve transection.

FIG. 4 shows that GPI 1046 treatment duration significantly affects the process of optic nerve axonal degeneration after transection.

FIG. 5 shows that GPI 1046 treatment produces a greater effect on optic nerve axons than ganglion cell bodies.

FIG. 6 shows that GPI 1046 treatment for 28 days after optic nerve transection prevents myelin degeneration in the proximal stump.

FIG. 8 shows GPI 1046 treatment for 28 days after optic nerve transection prevents myelin degeneration in the distal stump.

FIG. 9 shows that 28 day treatment with GPI 1046 treatment beginning 8 weeks after onset of streptozotocin induced diabetes decreases the extent of neovascularization in the inner and outer retina and protects neurons in the inner nuclear layer (INL) and ganglion cell layer (GCL) from degeneration.

DETAILED DESCRIPTION OF THE INVENTION

Definitions

Figure 2:
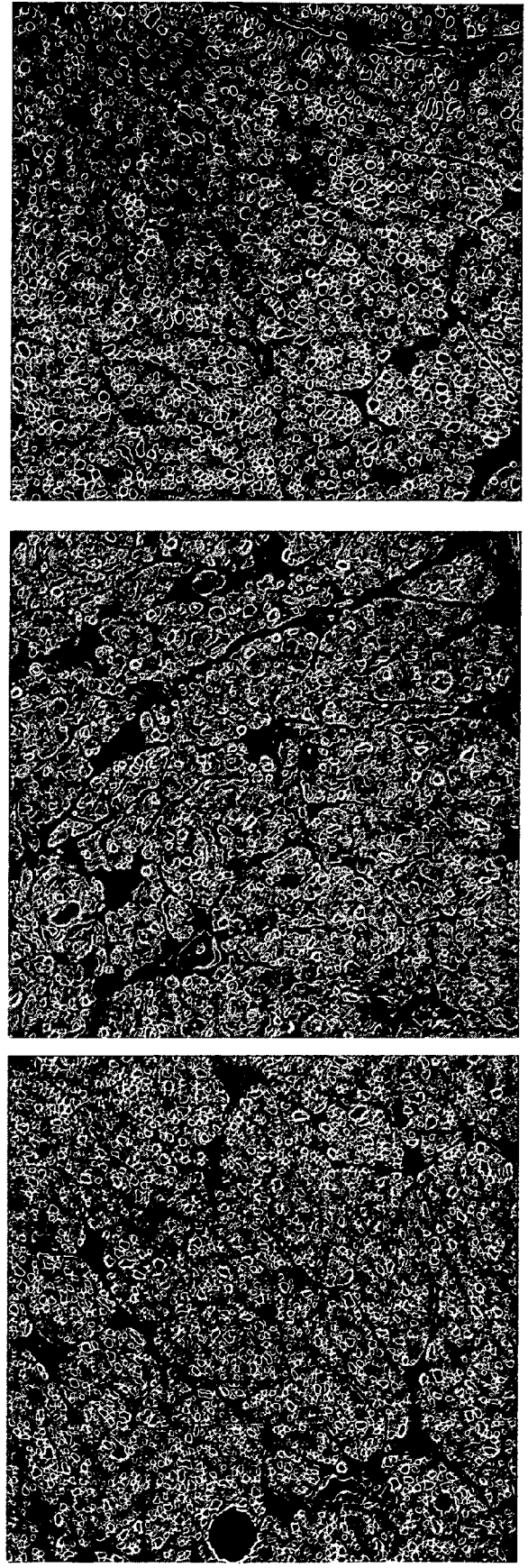
FIG. 2 shows that GPI 1046 prevents degeneration of optic nerve axons and myelin following retinal ischemia.

"Eye" refers to the anatomical structure responsible for vision in humans and other animals, and encompasses the following anatomical structures, without limitation: lens, vitreous body, ciliary body, posterior chamber, anterior chamber, pupil, cornea, iris, canal of Schlemm, zonules of Zinn, limbus, conjunctiva, choroid, retina, central vessels of the retina, optic nerve, fovea centralis, macula lutea, and sclera.

"Alkyl" means a branched or unbranched saturated hydrocarbon chain comprising a designated number of carbon atoms. For example, $C_1$–$C_6$ straight or branched alkyl hydrocarbon chain contains 1 to 6 carbon atoms, and includes but is not limited to substituents such as methyl, ethyl, propyl, iso-propyl, butyl, iso-butyl, tert-butyl, n-pentyl, n-hexyl, and the like. It is also contemplated as within the scope of the present invention that "alkyl" may also refer to a hydrocarbon chain wherein any of the carbon atoms of said alkyl are optionally replaced with O, NH, S, or $SO_2$. For example, carbon 2 of n-pentyl can be replaced with O to form propyloxymethyl.

"Alkenyl" means a branched or unbranched unsaturated hydrocarbon chain comprising a designated number of carbon atoms. For example, $C_2$–$C_6$ straight or branched alkenyl hydrocarbon chain contains 2 to 6 carbon atoms having at least one double bond, and includes but is not limited to substituents such as ethenyl, propenyl, iso-propenyl, butenyl, iso-butenyl, tert-butenyl, n-pentenyl, n-hexenyl, and the like. It is also contemplated as within the scope of the present invention that "alkenyl" may also refer to an unsaturated hydrocarbon chain wherein any of the carbon atoms of said alkenyl are optionally replaced with O, NH, S, or $SO_2$. For example, carbon 2 of 4-pentene can be replaced with O to form (2propene)oxymethyl.

"Alkoxy" means the group —OR wherein R is alkyl as herein defined. Preferably, R is a branched or unbranched saturated hydrocarbon chain containing 1 to 6 carbon atoms.

"Aryl, heteroaryl, carbocycle, or heterocycle" includes but is not limited to cyclic or fused cyclic ring moieties and includes a mono-, bi- or tricyclic, carbo- or heterocyclic ring, wherein the ring is either unsubstituted or substituted in one or more position(s) with hydroxy, carbonyl, amino, amido, cyano, isocyano, nitro, nitroso, nitrilo, isonitrilo, imino, azo, diazo, sulfonyl, sulfhydryl, sulfoxy, thio, thiocarbonyl, thiocyano, formanilido, thioformamido, sulfhydryl, halo, haloalkyl; trifluoromethyl, alkoxy, alkenoxy, alkylaryloxy, aryloxy, arylalkyloxy, alkylamino, aminoalkyl, thioalkyl, alkylthio, $C_1$–$C_6$ straight or branched chain alkyl, $C_2$–$C_6$ straight or branched chain alkenyl or alkynyl, aryl, heteroaryl, carbocycle, heterocycle, or $CO_2R^4$ where $R^4$ is hydrogen or $C_1$–$C_9$ straight or branched chain alkyl and carbocyclic and heterocyclic moieties; wherein the individual ring sizes are 5–8 members; wherein the heterocyclic ring contains 1–4 heteroatom(s) selected from the group consisting of O, N, or S; wherein aromatic or tertiary alkyl amines are optionally oxidized to a corresponding N-oxide. Examples of useful alkyl groups include, without limitation, methyl, ethyl, propyl, isopropyl, butyl, tert-butyl, n-pentyl, 2-methyl pentyl and the like. Examples of useful carbocyclic and heterocyclic moieties include, without limitation, phenyl, benzyl, naphthyl, indenyl, azulenyl, fluorenyl, anthracenyl, indolyl, isoindolyl, indolinyl, benzofuranyl, benzothiophenyl, indazolyl, benzimidazolyl, benzthiazolyl, tetrahydrofuranyl, tetrahydropyranyl, pyridyl, pyrrolyl, pyrrolidinyl, pyridinyl, pyrimidinyl, purinyl, quinolinyl, isoquinolinyl, tetrahydroquinolinyl, quinolizinyl, furyl, thiophenyl, imidazolyl, oxazolyl, benzoxazolyl, thiazolyl, isoxazolyl, isotriazolyl, oxadiazolyl, triazolyl, thiadiazolyl, pyridazinyl, pyrimidinyl, pyrazinyl, triazinyl, trithianyl, indolizinyl, pyrazolyl, pyrazolinyl, pyrazolidinyl, thienyl, tetrahydroisoquinolinyl, cinnolinyl, phthalazinyl, quinazolinyl, quinoxalinyl, naphthyridinyl, pteridinyl, carbazolyl, acridinyl, phenazinyl, phenothiazinyl, phenoxazinyl, and adamantyl.

"Halo" means at least one fluoro, chloro, bromo, or iodo moiety.

The term "pharmaceutically acceptable salt, ester, or solvate" refers to salt, ester, or solvates of the subject compounds which possess the desired pharmacological activity and which are neither biologically nor otherwise undesirable. The salt, ester, or solvates can be formed with inorganic or organic acids such as acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, gluconate, glycerophosphate, hemisulfate, heptanoate, hexanoate, hydrochloride hydrobromide, hydroiodide, 2-hydroxyethanesulfonate, lactate, maleate, methanesulfonate, naphthylate, 2-naphthalenesulfonate, nicotinate, oxalate, sulfate, thiocyanate, tosylate and undecanoate. Base salt, ester, or solvates include ammonium salts, alkali metal salts such as lithium, sodium and potassium salts, alkaline earth metal salts such as calcium and magnesium salts, salt with organic bases such as dicyclohexylamine salts, N-methyl-D-glucamine, and salts with amino acids such as arginine, lysine, and so forth. Also, the basic nitrogen-containing groups can be quaternized with such agents as: 1) lower alkyl halides, such as methyl, ethyl, propyl, and butyl chloride, bromides and iodides; 2) dialkyl sulfates like dimethyl, diethyl, dibutyl and diamyl sulfates; 3) long chain alkyls such as decyl, lauryl, myristyl and stearyl substituted with one or more halide such as chloride, bromide and iodide; and 4) aralkyl halides like benzyl and phenethyl bromide and others.

The compounds of this invention may possess at least one asymmetric center and thus can be produced as mixtures of stereoisomers or as individual enantiomers or diastereomers. The individual stereoisomers may be obtained by using an optically active starting material, by resolving a racemic or non-racemic mixture of an intermediate at some appropriate stage of the synthesis, or by resolution of the compound of formula (I). It is understood that the individual stereoisomers as well as mixtures (racemic and non-racemic) of stereoisomers are encompassed by the scope of the present invention. The S-stereoisomer at atom 1 of formula I is a most preferred embodiment of the invention.

"Stereoisomers" are isomers that differ only in the way the atoms are arranged in space.

"Isomers" are different compounds that have the same molecular formula and includes cyclic isomers such as (iso)indole and other isomeric forms of cyclic moieties.

"Enantiomers" are a pair of stereoisomers that are non-superimposable mirror images of each other.

"Diastereoisomers" are stereoisomers which are not mirror images of each other.

"Racemic mixture" means a mixture containing equal parts of individual enantiomers. "Non-racemic mixture" is a mixture containing unequal parts of individual enantiomers or stereoisomers.

"Isosteres" are different compounds that have different molecular formulae but exhibit the same or similar properties. For example, tetrazole is an isostere of carboxylic acid because it mimics the properties of carboxylic acid even though they both have very different molecular formulae. Tetrazole is one of many possible isosteric replacements for carboxylic acid. Other carboxylic acid isosteres contemplated by the present invention include —COOH, —SO$_3$H, —SO$_2$HNR$^3$, —PO$_2$(R$^3$)$_2$, —CN, —PO$_3$(R$^3$)$_2$, —OR$^3$, —SR$^3$, —NHCOR$^3$, —N(R$^3$)$_2$, —CON(R)$_2$, —CONH(O)R$^3$, —CONHNHSO$_2$R$^3$, —COHNSO$_2$R$^3$, and —CONR$^3$CN. In addition, carboxylic acid isosteres can include 5–7 membered carbocycles or heterocycles containing any combination of CH$_2$, O S, or N in any chemically stable oxidation state, where any of the atoms of said ring structure are optionally substituted in one or more positions. The following structures are non-limiting examples of preferred carbocyclic and heterocyclic isosteres contemplated by this invention.

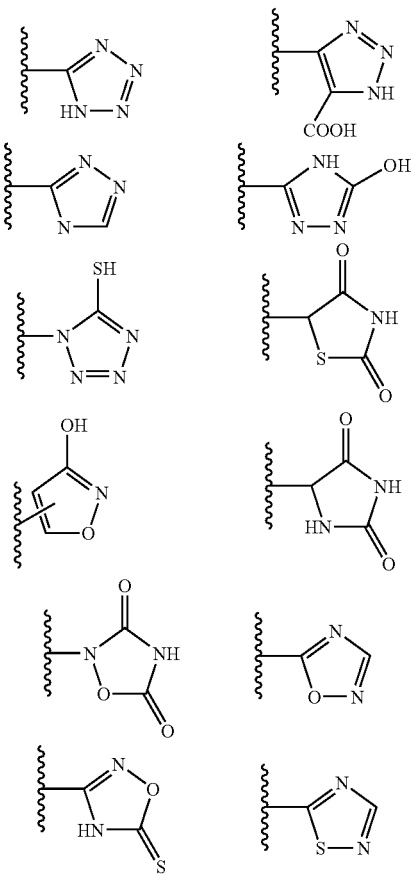

-continued

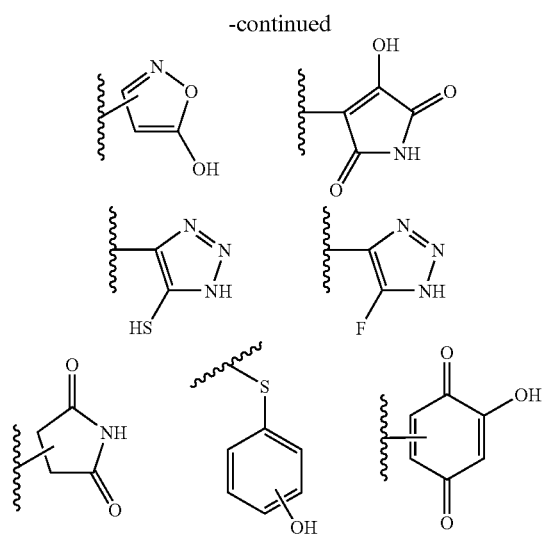

where the atoms of said ring structure may be optionally substituted at one or more positions with $R^3$. The present invention contemplates that when chemical substituents are added to a carboxylic isostere then the inventive compound retains the properties of a carboxylic isostere. The present invention contemplates that when a carboxylic isostere is optionally substituted with one or more moieties selected from $R^3$, then the substitution cannot eliminate the carboxylic acid isosteric properties of the inventive compound. The present invention contemplates that the placement of one or more $R^1$ substituents upon a carbocyclic or heterocyclic carboxylic acid isostere shall not be permitted at one or more atom(s) which maintain(s) or is/are integral to the carboxylic acid isosteric properties of the inventive compound, if such substituent(s) would destroy the carboxylic acid isosteric properties of the inventive compound.

Other carboxylic acid isosteres not specifically exemplified or described in this specification are also contemplated by the present invention.

The term "preventing neurodegeneration" as used herein includes the ability to inhibit or prevent neurodegeneration in patients newly diagnosed as having a neurodegenerative disease, or at risk of developing a new degenerative disease and for inhibiting or preventing further neurodegeneration in patients who are already suffering from or have symptoms of a neurodegenerative disease.

The term "treatment" as used herein covers any treatment of a disease and/or condition in an animal, particularly a human, and includes:

(i) preventing a disease and/or condition from occurring in a subject which may be predisposed to the disease and/or condition but has not yet been diagnosed as having it;

(ii) inhibiting the disease and/or condition, i.e., arresting its development; or (iii) relieving the disease and/or condition, i.e., causing regression of the disease and/or condition.

The system used in naming the compounds of the present invention is shown below, using a compound of formula I as an example.

A compound of the present invention, especially formula I, wherein n is 1, X is O, D is a bond, $R_1$ is 1,1, dimethylpropyl, and $R_2$ is —CN, is named (2S)-1-(1,2-dioxo-3,3-dimethylpentyl)-2-pyrrolidinecarbonitrile.

"Enhancing memory performance" refers to improving or increasing the mental faculty by which to register, retain or recall past experiences, knowledge, ideas, sensations, thoughts or impressions.

"Memory impairment" refers to a diminished mental registration, retention or recall of past experiences, knowledge, ideas, sensations, thoughts or impressions. Memory impairment may affect short and long-term information retention, facility with spatial relationships, memory (rehearsal) strategies, and verbal retrieval and production. Common causes of memory impairment are age, severe head trauma, brain anoxia or ischemia, alcoholic-nutritional diseases, and drug intoxications. Examples of memory impairment include, without limitation, benign forgetfulness, amnesia and any disorder in which memory deficiency is present, such as Korsakoff's amnesic psychosis, dementia and learning disorders.

"Neopsic factors" or "neopsics" refers to compounds useful in treating vision loss, preventing vision degeneration, or promoting vision regeneration.

"Neopsis" refers to the process of treating vision loss, preventing vision degeneration, or promoting vision regeneration.

"Ophthalmological" refers to anything about or concerning the eye, without limitation, and is used interchangeably with "ocular," "ophthalmic," "ophthalmologic," and other such terms, without limitation.

"Preventing vision degeneration" refers to the ability to prevent degeneration of vision in patients newly diagnosed as having a degenerative disease affecting vision, or at risk of developing a new degenerative disease affecting vision, and for preventing further degeneration of vision in patients who are already suffering from or have symptoms of a degenerative disease affecting vision.

"Promoting vision regeneration" refers to maintaining, improving, stimulating or accelerating recovery of, or revitalizing one or more components of the visual system in a manner which improves or enhances vision, either in the presence or absence of any ophthalmologic disorder, disease, or injury.

"Treating" refers to:

(i) preventing a disease and/or condition from occurring in a subject which may be predisposed to the disease and/or condition but has not yet been diagnosed as having it;

(ii) inhibiting the disease and/or condition, i.e., arresting its development; or (iii) relieving the disease and/or condition, i.e., causing regression of the disease and/or condition.

"Vision" refers to the ability of humans and other animals to process images, and is used interchangeably with "sight", "seeing", and other such terms, without limitation.

"Vision disorder" refers to any disorder that affects or involves vision, including without limitation visual impairment, orbital disorders, disorders of the lacrimal apparatus, disorders of the eyelids, disorders of the conjunctiva, disorders of the cornea, cataracts, disorders of the uveal tract, disorders of the retina, disorders of the optic nerve or visual pathways, free radical induced eye disorders and diseases, immunologically-mediated eye disorders and diseases, eye injuries, and symptoms and complications of eye disease, eye disorder, or eye injury.

"Visual impairment" refers to any dysfunction in vision including without limitation disturbances or diminution in vision (e.g., binocular, central, peripheral, scotopic), visual acuity for objects near and far, visual field, ocular motility, color perception, adaptation to light and dark, accommodation, refraction, and lacrimation. See Physician's Desk Reference (PDR) for Ophthalmology, 16th Edition, 6:47 (1988).

Methods of the Present Invention

The present invention relates to a method of treating a vision disorder, improving vision, treating memory impairment, or enhancing memory performance in an animal, which comprises administering to said animal an effective amount of a derivative.

The inventive methods are particularly useful for treating various eye disorders including but not limited to visual disorders, diseases, injuries, and complications, genetic disorders; disorders associated with aging or degenerative vision diseases; vision disorders correlating to physical injury to the eye, head, or other parts of the body resulting from external forces; vision disorders resulting from environmental factors; vision disorders resulting from a broad range of diseases; and combinations of any of the above.

In particular, the compositions and methods of the present invention are useful for improving vision, or correcting, treating, or preventing visual (ocular) impairment or dysfunction of the visual system, including permanent and temporary visual impairment, without limitation. The present invention is also useful in preventing and treating ophthalmologic diseases and disorders, treating damaged and injured eyes, and preventing and treating diseases, disorders, and injuries which result in vision deficiency, vision loss, or reduced capacity to see or process images, and the symptoms and complications resulting from same. The eye diseases and disorders which may be treated or prevented by the compositions and methods of the present invention are not limited with regard to the cause of said diseases or disorders. Accordingly, said compositions and methods are applicable whether the disease or disorder is caused by genetic or environmental factors, as well as any other influences. The compositions and methods of the present invention are particularly useful for eye problems or vision loss or deficiency associated with all of the following, without limitation: aging, cellular or physiological degeneration, central nervous system or neurological disorder, vascular defects, muscular defects, and exposure to adverse environmental conditions or substances.

The compositions and methods of the present invention are particularly useful in correcting, treating, or improving visual impairment, without limitation. Visual impairment in varying degrees occurs in the presence of a deviation from normal in one or more functions of the eye, including (1) visual acuity for objects at distance and near; (2) visual fields; and (3) ocular motility without diplopia. See *Physicians' Desk Reference (PDR) for Ophthalmology*, 16th Edition, 6:47 (1988). Vision is imperfect without the coordinated function of all three. Id.

Said compositions and methods of use are also useful in correcting, treating, or improving other ocular functions including, without limitation, color perception, adaptation to light and dark, accommodation, metamorphopsia, and binocular vision. The compositions and methods of use are particularly useful in treating, correcting, or preventing ocular disturbances including, without limitation, paresis of accommodation, iridoplegia, entropion, ectropion, epiphora, lagophthalmos, scarring, vitreous opacities, non-reactive pupil, light scattering disturbances of the cornea or other media, and permanent deformities of the orbit.

The compositions and methods of use of the present invention are also highly useful in improving vision and treating vision loss. Vision loss ranging from slight loss to absolute loss may be treated or prevented using said compositions and methods of use. Vision may be improved by the treatment of eye disorders, diseases, and injuries using the compositions and methods of the invention. However, improvements in vision using the compositions and methods of use are not so limited, and may occur in the absence of any such disorder, disease, or injury.

The compositions and methods of the present invention are also useful in the treatment or prevention of the following non-limiting exemplary diseases and disorders, and symptoms and complications resulting therefrom.

Vision disorders include but are not limited to the following:

visual impairment, such as diminished visual acuity for objects near and far, visual fields, and ocular motility;

orbital disorders, such as orbital cellulitis, periorbital cellulitis, cavernous sinus thrombosis, and exophthalmos (proptosis);

disorders of the lacrimal apparatus, such as dacryostenosis, congenital dacryostenosis, and dacryocystitis (acute or chronic);

disorders of the eyelids, such as lid edema, blepharitis, ptosis, Bell's palsy, blepharospasm, hordeolum (stye), external hordeolum, internal hordeolum (meibomian stye), chalazion, entropion (inversion of the eyelid), ectropion (eversion of the eyelid), tumors (benign and malignant), xanthelasma, basil cell carcinoma, squamous cell carcinoma, meibomian gland carcinoma, and melanoma;

disorders of the conjunctiva, such as pinguecula, pterygium, and other neoplasms, acute conjunctivitis, chronic conjunctivitis, adult gonococcal conjunctivitis, neonatal conjunctivitis, trachoma (granular conjunctivitis or Egyptian ophthalmia), inclusion conjunctivitis (inclusion blenorrhea or swimming pool conjunctivitis), neonatal inclusion conjunctivitis, adult inclusion conjunctivitis, vernal keratoconjunctivitis, keratoconjunctivitis sicca (keratitis sicca or dry eye syndrome), episcleritis, scleritis, cicatricial pemphigoid (ocular cicatricial pemphigoid or benign mucous membrane pemphigoid), and subconjunctival hemorrhage;

disorders of the cornea, such as superficial punctate keratitis, corneal ulcer, indolent ulcer, recurrent corneal erosion, corneal epithelial basement membrane dystrophy, corneal endothelial cell dystrophy, herpes simplex keratitis (herpes simplex keratoconjunctivitis), dendritic keratitis, disciform keratitis, ophthalmic herpes zoster, phlyctenular keratoconjunctivitis (phlyctenular or eczematous conjunctivitis), interstitial keratitis (parenchymatous keratitis), peripheral ulcerative keratitis (marginal keratolysis or peripheral rheumatoid ulceration), keratomalacia (xerotic keratitis), xerophthalmia, keratoconus, bullous keratopathy;

cataracts, including developmental or congenital cataracts, juvenile or adult cataracts, nuclear cataract, posterior subcapsular cataracts;

disorders of the uveal tract, such as uveitis (inflammation of the uveal tract or retina), anterior uveitis, intermediate uveitis, posterior uveitis, iritis, cyclitis, choroiditis, ankylosing spondylitis, Reiter's syndrome, pars planitis, toxoplasmosis, cytomegalovirus (CMV), acute retinal necrosis, toxocariasis, birdshot choroidopathy, histoplasmosis (presumed ocular histoplasmosis syndrome), Behcet's syndrome, sympathetic ophthalmia, Vogt-Koyanagi-Harada syndrome, sarcoidosis, reticulum cell sarcoma, large cell lymphoma, syphilis, tuberculosis, juvenile rheumatoid arthritis, endophthalmitis, and malignant melanoma of the choroid;

disorders of the retina, such as vascular retinopathies (e.g., arteriosclerotic retinopathy and hypertensive retinopathy), central and branch retinal artery occlusion, central and branch retinal vein occlusion, diabetic retinopathy (e.g., proliferative retinopathy and non-proliferative retinopathy), macular degeneration of the aged (age-related macular degeneration or senile macular degeneration), neovascular macular degeneration, retinal detachment, retinitis pigmentosa, retinal photic injury, retinal ischemia-induced eye injury, and glaucoma (e.g., primary glaucoma, chronic open-angle glaucoma, acute or chronic angle-closure, congenital (infantile) glaucoma, secondary glaucoma, and absolute glaucoma);

disorders of the optic nerve or visual pathways, such as papilledema (choked disk), papillitis (optic neuritis), retrobulbar neuritis, ischemic optic neuropathy, toxic amblyopia, optic atrophy, higher visual pathway lesions, disorders of ocular motility (e.g., third cranial nerve palsies, fourth cranial nerve palsies, sixth cranial nerve palsies, internuclear ophthalmoplegia, and gaze palsies);

free radical induced eye disorders and diseases; and immunologically-mediated eye disorders and diseases, such as Graves' ophthalmopathy, conical cornea, dystrophia epithelialis corneae, corneal leukoma, ocular pemphigus, Mooren's ulcer, scleritis, and sarcoidosis (See *The Merck Manual*, Sixteenth Edition, 217:2365–2397 (1992) and *The Eye Book*, Cassel, Billig, and Randall, The Johns Hopkins University Press (1998)).

The compositions and methods of the present invention are also useful in the treatment of the following non-limiting eye injuries, and symptoms and complications resulting therefrom: conjunctival and corneal foreign body injuries, corneal abrasion, intraocular foreign body injuries, lacerations, lid lacerations, contusions, lid contusions (black eye), trauma to the globe, laceration of the iris, cataract, dislocated lens, glaucoma, vitreous hemorrhage, orbital-floor fractures, retinal hemorrhage or detachment, and rupture of the eyeball, anterior chamber hemorrhage (traumatic hyphema), burns, eyelid burns, chemical burns, chemical burns of the cornea and conjunctiva, and ultraviolet light burns (sunburn). See *The Merck Manual, Sixteenth Edition*, 217: 2364–2365 (1992).

The compositions and methods of the present invention are also useful in treating and/or preventing the following non-limiting exemplary symptoms and complications of eye disease, eye disorder or eye injury: subconjunctival hemorrhages, vitreous hemorrhages, retinal hemorrhages, floaters, retinal detachments, photophobia, ocular pain, scotomas (negative and positive), errors of refraction, emmetropia, ametropia, hyperopia (farsightedness), myopia (nearsightedness), astigmatism, anisometropia, aniseikonia, presbyopia, bleeding, recurrent bleeding, sympathetic ophthalmia, inflammation, swelling, redness of the eye, irritation of the eye, corneal ulceration and scarring, iridocyclitis, perforation of the globe, lid deformities, exophthalmos, impaired mobility of the eye, lid swelling, chemosis, loss of vision, including partial or total blindness, optic neuritis, fever, malaise, thrombophlebitis, cavernous sinus thrombosis, panophthalmitis, infection of the meninges and brain, papilledema, severe cerebral symptoms (headache, decreased level of consciousness, and convulsions), cranial nerve palsies, epiphora (chronic or persistent tearing), copious reflux of mucus or pus, follicular subconjunctival hyperplasia, corneal vascularization, cicatrization of the conjunctiva, cornea, and lids, pannus, hypopyon, lagophthalmos, phlyctenules, rubeosis iridis, bitemporal hemianopia, and homonymous hemianopia. See *The Merck Manual, Sixteenth Edition*, 217:2362–2363 (1992).

The derivative may be administered in combination with an effective amount of one or more factor(s) useful in treating vision disorder, improving vision, treating memory impairment, or enhancing memory performance.

In a preferred embodiment, the factor(s) to be combined with the derivative is/are selected from the group consisting of immunosuppressants for treating autoimmune, inflammatory, and immunologically-mediated disorders; wound healing agents for treating wounds resulting from injury or surgery; antiglaucomatous medications for treating abnormally elevated intraocular pressure; neurotrophic factors and growth factors for treating neurodegenerative disorders or stimulating neurite outgrowth; compounds effective in limiting or preventing hemorrhage or neovascularization for treating macular degeneration; and antioxidants for treating oxidative damage to eye tissues.

Pharmaceutical Compositions of the Present Invention

The present invention also relates to a pharmaceutical composition comprising:

(i) an effective amount of a derivative for treating a vision disorder, improving vision, treating memory impairment, or enhancing memory performance in an animal; and (ii) a pharmaceutically acceptable carrier.

The derivative may be administered in combination with an effective amount of one or more factor(s) useful in treating vision disorders, improving vision, treating memory impairment, or enhancing memory performance.

TABLE A

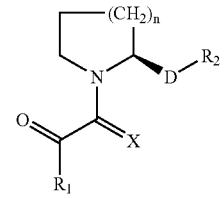

when D is a bond and R2 is COOH,

| No. | X | n | $R_1$ |
|---|---|---|---|
| 1 | O | 1 | 3,4,5-trimethylphenyl |
| 2 | O | 2 | 3,4,5-trimethylphenyl |
| 3 | O | 1 | tert-butyl |
| 4 | O | 3 | tert-butyl |
| 5 | O | 1 | cyclopentyl |
| 6 | O | 2 | cyclopentyl |
| 7 | O | 3 | cyclopentyl |
| 8 | O | 1 | cyclohexyl |
| 9 | O | 2 | cyclohexyl |
| 10 | O | 3 | cyclohexyl |
| 11 | O | 1 | cycloheptyl |
| 12 | O | 2 | cycloheptyl |
| 13 | O | 3 | cycloheptyl |
| 14 | O | 1 | 2-thienyl |
| 15 | O | 2 | 2-thienyl |
| 16 | O | 3 | 2-thienyl |
| 17 | O | 1 | 2-furyl |
| 18 | O | 2 | 2-furyl |
| 19 | O | 3 | 2-furyl |
| 20 | O | 3 | phenyl |
| 21 | O | 1 | 1,1-dimethylpentyl |
| 22 | O | 2 | 1,1-dimethylhexyl |
| 23 | O | 3 | ethyl |

TABLE B

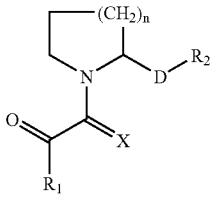

| No. | X | n | R₁ | D | R₂ |
|---|---|---|---|---|---|
| 24 | S | 1 | 1,1-dimethyl propyl | $CH_2$ | COOH |
| 25 | S | 1 | 1,1-dimethyl propyl | bond | COOH |
| 26 | O | 1 | 1,1-dimethyl propyl | $CH_2$ | OH |
| 27 | O | 1 | 1,1-dimethyl propyl | bond | $SO_3H$ |
| 28 | O | 1 | 1,1-dimethyl propyl | $CH_2$ | CN |
| 29 | O | 1 | 1,1-dimethyl propyl | bond | CN |
| 30 | O | 1 | 1,1-dimethyl propyl | bond | tetrazolyl |
| 31 | S | 1 | phenyl | $(CH_2)_2$ | COOH |
| 32 | S | 1 | phenyl | $(CH_2)_3$ | COOH |
| 33 | S | 2 | phenyl | $CH_2$ | COOH |
| 34 | O | 1 | 1,1-dimethyl propyl | bond | $CONH_2$ |
| 35 | O | 2 | 1,1-dimethyl propyl | bond | $CONH_2$ |
| 36 | S | 2 | 2-furyl | bond | $PO_3H_2$ |
| 37 | O | 2 | propyl | $(CH_2)_2$ | COOH |
| 38 | O | 2 | propyl | $(CH_2)_3$ | COOH |
| 39 | O | 1 | tert-butyl | $(CH_2)_4$ | COOH |
| 40 | O | 1 | methyl | $(CH_2)_5$ | COOH |
| 41 | O | 2 | phenyl | $(CH_2)_6$ | COOH |
| 42 | O | 2 | 3,4,5-trimethoxyphenyl | $CH_2$ | COOH |
| 43 | O | 2 | 3,4,5-trimethoxyphenyl | $CH_2$ | tetrazolyl |

TABLE C

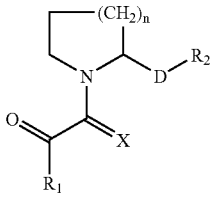

| No. | n | X | D | R₂ | R₁ |
|---|---|---|---|---|---|
| 44 | 1 | S | bond | COOH | Phenyl |
| 45 | 1 | O | bond | COOH | α-MethylBenzyl |
| 46 | 2 | O | bond | COOH | 4-MethylBenzyl |
| 47 | 1 | O | bond | Tetrazole | Benzyl |
| 48 | 1 | O | bond | $SO_3H$ | α-MethylBenzyl |
| 49 | 1 | O | $CH_2$ | COOH | 4-MethylBenzyl |
| 50 | 1 | O | bond | $SO_2HNMe$ | Benzyl |
| 51 | 1 | O | bond | CN | α-MethylBenzyl |
| 52 | 1 | O | bond | $PO_3H_2$ | 4-MethylBenzyl |
| 53 | 2 | O | bond | COOH | Benzyl |
| 54 | 2 | O | bond | COOH | α-MethylBenzyl |
| 55 | 2 | O | bond | COOH | 4-MethylBenzyl |
| 56 | 2 | S | bond | COOH | 3,4,5-trimethoxy phenyl |
| 57 | 2 | O | bond | COOH | Cyclohexyl |
| 58 | 2 | O | bond | $PO_2HEt$ | i-propyl |
| 59 | 2 | O | bond | $PO_3HPropyl$ | ethyl |
| 60 | 2 | O | bond | $PO_3(Et)_2$ | Methyl |
| 61 | 2 | O | bond | OMe | tert-butyl |
| 62 | 1 | O | bond | OEt | n-pentyl |
| 63 | 2 | O | bond | OPropyl | n-hexyl |
| 64 | 1 | O | bond | OButyl | Cyclohexyl |
| 65 | 1 | O | bond | OPentyl | cyclopentyl |
| 66 | 1 | O | bond | OHexyl | n-heptyl |
| 67 | 1 | O | bond | SMe | n-octyl |
| 68 | 1 | O | bond | SEt | n-nonyl |
| 69 | 2 | O | bond | SPropyl | 2-indolyl |
| 70 | 2 | O | bond | SButyl | 2-furyl |
| 71 | 2 | O | bond | NHCOMe | 2-thiazolyl |

TABLE C-continued

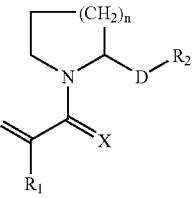

| No. | n | X | D | R₂ | R₁ |
|---|---|---|---|---|---|
| 72 | 2 | O | bond | NHCOEt | 2-thienyl |
| 73 | 1 | O | $CH_2$ | $N(Me)_2$ | 2-pyridyl |
| 74 | 1 | O | $(CH_2)_2$ | N(Me)Et | 1,1-dimethylpropyl |
| 75 | 1 | O | $(CH_2)_3$ | $CON(Me)_2$ | 1,1-dimethylpropyl |
| 76 | 1 | O | $(CH_2)_4$ | CONHMe | 1,1-dimethylpropyl |
| 77 | 1 | O | $(CH_2)_5$ | CONHEt | 1,1-dimethylpropyl |
| 78 | 1 | O | $(CH_2)_6$ | CONHPropyl | 1,1-dimethylpropyl |
| 79 | 1 | O | bond | CONH(O)Me | Benzyl |
| 80 | 1 | O | bond | CONH(O)Et | α-Methylphenyl |
| 81 | 1 | O | bond | CONH(O)Propyl | 4-Methylphenyl |
| 82 | 1 | O | $(CH_2)_2$ | COOH | Benzyl |
| 83 | 1 | O | bond | COOH | α-Methylphenyl |
| 84 | 1 | O | bond | COOH | 4-Methylphenyl |
| 85 | 1 | O | $CH_2$ | COOH | 1,1-dimethylpropyl |
| 86 | 1 | O | $(CH_2)_2$ | COOH | 1,1-dimethylbutyl |
| 87 | 1 | O | $(CH_2)_3$ | COOH | 1,1-dimethylpentyl |
| 88 | 1 | O | $(CH_2)_4$ | COOH | 1,1-dimethylhexyl |
| 89 | 1 | O | $(CH_2)_5$ | COOH | 1,1-dimethylethyl |
| 90 | 1 | O | $(CH_2)_6$ | COOH | iso-propyl |
| 91 | 1 | O | $(CH_2)_7$ | COOH | tert-butyl |
| 92 | 1 | O | $(CH_2)_8$ | COOH | 1,1-dimethylpropyl |
| 93 | 1 | O | $(CH_2)_9$ | COOH | benzyl |
| 94 | 1 | O | $(CH_2)_{10}$ | COOH | 1,1-dimethylpropyl |
| 95 | 1 | O | $C_2H_2$ | COOH | cyclohexylmethyl |
| 96 | 1 | O | 2-OH, Et | COOH | 1,1-dimethylpropyl |
| 97 | 1 | O | 2-butylene | COOH | 1,1-dimethylpropyl |
| 98 | 1 | S | i-Pro | COOH | 1,1-dimethylpropyl |
| 99 | 2 | S | tert-Bu | COOH | phenyl |
| 100 | 2 | O | 2-nitro-hexyl | COOH | 1,1-dimethylpropyl |
| 101 | 1 | O | $(CH_2)_2$ | CN | 1,1-dimethylpropyl |
| 102 | 1 | O | $(CH_2)_3$ | CN | 1,1-dimethylpropyl |
| 103 | 3 | O | bond | $CONHNHSO_2Me$ | Benzyl |
| 104 | 3 | O | bond | $CONHNHSO_2Et$ | α-Methylphenyl |
| 105 | 3 | O | bond | $CONHSO_2Me$ | 4-Methylphenyl |
| 106 | 1 | O | bond | $CONHNHSO_2Et$ | Phenyl |
| 107 | 2 | O | bond | CON(Me)CN | α-Methylphenyl |
| 108 | 1 | O | bond | CON(Et)CN | 4-Methylphenyl |
| 109 | 1 | O | $(CH_2)_2$ | COOH | methyl |
| 110 | 1 | O | $(CH_2)_3$ | COOH | ethyl |
| 111 | 1 | O | $(CH_2)_4$ | COOH | n-propyl |
| 112 | 1 | O | $(CH_2)_5$ | COOH | t-butyl |
| 113 | 1 | O | $(CH_2)_6$ | COOH | Pentyl |
| 114 | 1 | O | $(CH_2)_7$ | COOH | Hexyl |
| 115 | 1 | O | $(CH_2)_8$ | COOH | Septyl |
| 116 | 1 | O | $(CH_2)_9$ | COOH | Octyl |
| 117 | 1 | O | $C_2H_2$ | COOH | Cyclohexyl |

| No. | n | X | D | R2 | R1 |
|---|---|---|---|---|---|
| 118 | 2 | O | bond | 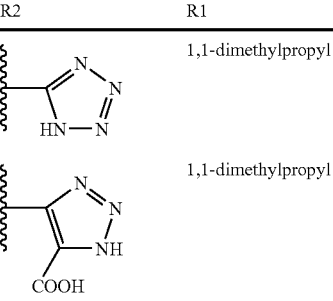 | 1,1-dimethylpropyl |
| 119 | 1 | O | bond | | 1,1-dimethylpropyl |

-continued

| No. | n | X | D | R2 | R1 |
|---|---|---|---|---|---|
| 120 | 1 | O | bond | 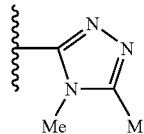 | 1,1-dimethylpropyl |
| 121 | 1 | O | bond | 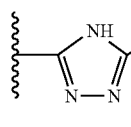 | 1,1-dimethylpropyl |
| 122 | 1 | O | bond | 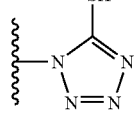 | 1,1-dimethylpropyl |
| 123 | 1 | O | bond | 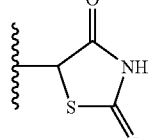 | 1,1-dimethylpropyl |
| 124 | 1 | O | bond | 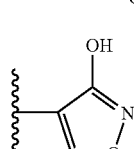 | 1,1-dimethylpropyl |
| 125 | 1 | O | bond | 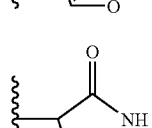 | 1,1-dimethylpropyl |
| 126 | 1 | O | bond | 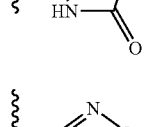 | 1,1-dimethylpropyl |
| 127 | 1 | O | bond | 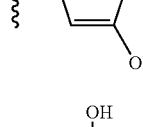 | 1,1-dimethylpropyl |
| 128 | 1 | O | bond | 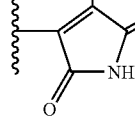 | 1,1-dimethylpropyl |
| 129 | 1 | O | bond | 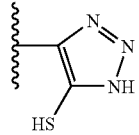 | 1,1-dimethylpropyl |

-continued

| No. | n | X | D | R2 | R1 |
|---|---|---|---|---|---|
| 130 | 1 | O | bond | 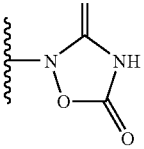 | 1,1-dimethylpropyl |
| 131 | 1 | O | bond | 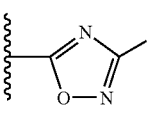 | 1,1-dimethylpropyl |
| 132 | 1 | O | bond | 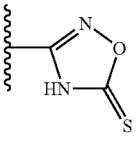 | 1,1-dimethylpropyl |
| 133 | 1 | O | bond | 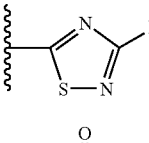 | 1,1-dimethylpropyl |
| 134 | 1 | O | bond | 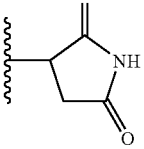 | 1,1-dimethylpropyl |
| 135 | 1 | O | bond | 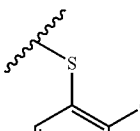 | 1,1-dimethylpropyl |
| 136 | 1 | O | bond | 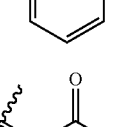 | 1,1-dimethylpropyl |
| 137 | 1 | O | bond | COOH | 1,1-dimethylpropyl |
| 138 | 2 | O | bond | COOH | 1,1-dimethylpropyl |

Affinity for FKBP12

The compounds used in the inventive methods and pharmaceutical compositions have an affinity for the FK506 binding protein, particularly FKBP12. The inhibition of the prolyl peptidyl cis-trans isomerase activity of FKBP may be measured as an indicator of this affinity.

$K_i$ Test Procedure

Inhibition of the peptidyl-prolyl isomerase (rotamase) activity of the compounds used in the inventive methods and pharmaceutical compositions can be evaluated by known methods described in the literature (Harding et al., *Nature*, 1989, 341:758–760; Holt et al. *J. Am. Chem. Soc.,* 115: 9923–9938). These values are obtained as apparent $K_i$'s.

The cis-trans isomerization of an alanine-proline bond in a model substrate, N-succinyl-Ala-Ala-Pro-Phe-p-nitroanilide, is monitored spectrophotometrically in a chymotrypsin-coupled assay, which releases para-nitroanilide from the trans form of the substrate. The inhibition of this reaction caused by the addition of different concentrations of inhibitor is determined, and the data is analyzed as a change in first-order rate constant as a function of inhibitor concentration to yield the apparent $K_i$ values.

In a plastic cuvette are added 950 ml of ice cold assay buffer (25 mM HEPES, pH 7.8, 100 mM NaCl), 10 ml of FKBP (2.5 mM in 10 mM Tris-Cl pH 7.5, 100 mM NaCl, 1 mM dithiothreitol), 25 ml of chymotrypsin (50 mg/ml in 1 mM HCl) and 10 ml of test compound at various concentrations in dimethyl sulfoxide. The reaction is initiated by the addition of 5 ml of substrate (succinyl-Ala-Phe-Pro-Phe-para-nitroanilide, 5 mg/ml in 2.35 mM LiCl in trifluoroethanol).

The absorbance at 390 nm versus time is monitored for 90 seconds using a spectrophotometer and the rate constants are determined from the absorbance versus time data files.

Route of Administration

To effectively treat vision loss or promote vision regeneration, the compounds used in the inventive methods and pharmaceutical compositions must readily affect the targeted areas. For these purposes, the compounds are preferably administered [topically to the skin.]

[For topical application to the skin, the compounds can be formulated into suitable ointments containing the compounds suspended or dissolved in, for example, mixtures with one or more of the following: mineral oil, liquid petrolatum, white petrolatum, propylene glycol, polyoxyethylene polyoxypropylene compound, emulsifying wax and water. Alternatively, the compounds can be formulated into suitable lotions or creams containing the active compound suspended or dissolved in, for example, a mixture of one or more of the following: mineral oil, sorbitan monostearate, polysorbate 60, cetyl ester wax, cetearyl alcohol, 2-octyldodecanol, benzyl alcohol and water.]

Other routes of administration known in the pharmaceutical art are also contemplated by this invention.

Dosage

Dosage levels on the order of about 0.1 mg to about 10,000 mg of the active ingredient compound are useful in the treatment of the above conditions, with preferred levels of about 0.1 mg to about 1,000 mg. The specific dose level for any particular patient will vary depending upon a variety of factors, including the activity of the specific compound employed; the age, body weight, general health, sex and diet of the patient; the time of administration; the rate of excretion; drug combination; the severity of the particular disease being treated; and the form of administration. Typically, in vitro dosage-effect results provide useful guidance on the proper doses for patient administration. Studies in animal models are also helpful. The considerations for determining the proper dose levels are well known in the art.

The compounds can be administered with other agents for treating vision loss, preventing vision degeneration, or promoting vision regeneration. Specific dose levels for such other agents will depend upon the factors previously stated and the effectiveness of the drug combination.

The following examples are illustrative of preferred embodiments of the invention and are not to be construed as limiting the invention thereto. All polymer molecular weights are mean average molecular weights. All percentages are based on the percent by weight of the final delivery system or formulation prepared unless otherwise indicated and all totals equal 100% by weight.

EXAMPLES

The inventive compounds may be prepared by a variety of synthetic sequences that utilize established chemical transformations. A general pathway to the present compounds is described in Scheme I. N-glyoxylproline derivatives may be prepared by reacting L-proline methyl ester with methyl oxalyl chloride as shown in Scheme I. The resulting oxamates may be reacted with a variety of carbon nucleophiles to obtain compounds used in the present invention.

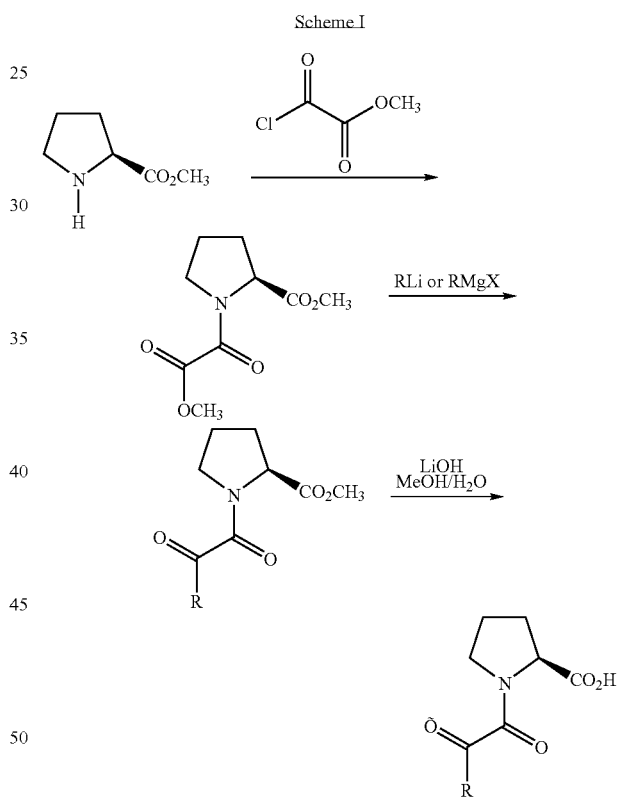

Example 1

Compound 137

Synthesis of (2S)-1-(3,3-dimethyl-1,2-dioxopentyl)-2-pyrrolidinecarboxylate a. Synthesis of (2S)-1-(1,2-dioxo-2-methoxyethyl)-2-pyrrolidinecarboxylate.

A solution of L-proline methyl ester hydrochloride (3.08 g; 18.60 mmol) in dry methylene chloride was cooled to 0° C. and treated with triethylamine (3.92 g; 38.74 mmol; 2.1 eq). After stirring the formed slurry under a nitrogen atmosphere for 15 min, a solution of methyl oxalyl chloride (3.20 g; 26.12 mmol) in methylene chloride (45 mL) was added dropwise. The resulting mixture was stirred at 0° C. for 1.5 hr. After filtering to remove solids, the organic phase was washed with water, dried over MgSO$_4$ and concentrated. The crude residue was purified on a silica gel column, eluting with 50% ethyl acetate in hexane, to obtain 3.52 g (88%) of the product as a reddish oil. Mixture of cis-trans amide rotamers; data for trans rotamer given. $^1$H NMR (CDCl$_3$): δ 1.93 (dm, 2H); 2.17 (m, 2H); 3.62 (m, 2H); 3.71 (s, 3H); 3.79, 3.84 (s, 3H total); 4.86 (dd, 1H, J=8.4, 3.3).

b. Synthesis of methyl (2S)-1-(1,2-dioxo-3,3-dimethylpentyl)-2-pyrrolidinecarboxylate.

A solution of methyl (2S)-1-(1,2-dioxo-2-methoxyethyl)-2-pyrrolidinecarboxylate (2.35 g; 10.90 mmol) in 30 mL of tetrahydrofuran (THF) was cooled to −78° C. and treated with 14.2 mL of a 1.0 M solution of 1,1-dimethylpropylmagnesium chloride in THF. After stirring the resulting homogeneous mixture at −78° C. for three hours, the mixture was poured into saturated ammonium chloride (100 mL) and extracted into ethyl acetate. The organic phase was washed with water, dried, and concentrated, and the crude material obtained upon removal of the solvent was purified on a silica gel column, eluting with 25% ethyl acetate in hexane, to obtain 2.10 g (75%) of the oxamate as a colorless oil. $^1$H NMR (CDCl$_3$): δ0.88 (t, 3H); 1.22, 1.26 (s, 3H each); 1.75 (dm, 2H); 1.87–2.10 (m, 3H); 2.23 (m, 1H); 3.54 (m, 2H); 3.76 (s, 3H); 4.52 (dm, 1H, J=8.4, 3.4).

c. Synthesis of (2S)-1-(1,2-dioxo-3,3-dimethylpentyl)-2-pyrrolidinecarboxylic acid (Compound 137).

A mixture of methyl (2S)-1-(1,2-dioxo-3,3-dimethylpentyl)-2-pyrrolidinecarboxylate (2.10 g; 8.23 mmol), 1 N LiOH (15 mL), and methanol (50 mL) was stirred at 0° C. for 30 min and at room temperature overnight. The mixture was acidified to pH 1 with 1 N HCl, diluted with water, and extracted into 100 mL of methylene chloride. The organic extract was washed with brine and concentrated to deliver 1.73 g (87%) of snow-white solid which did not require further purification. $^1$H NMR (CDCl$_3$): δ0.87 (t, 3H); 1.22, 1.25 (s, 3H each); 1.77 (dm, 2H); 2.02 (m, 2H); 2.17 (m, 1H); 2.25 (m, 1H); 3.53 (dd, 2H, J=10.4, 7.3); 4.55 (dd, 1H, J=8.6, 4.1).

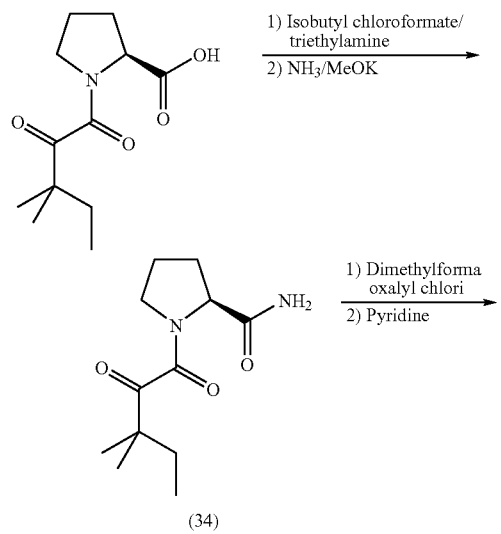

(34)

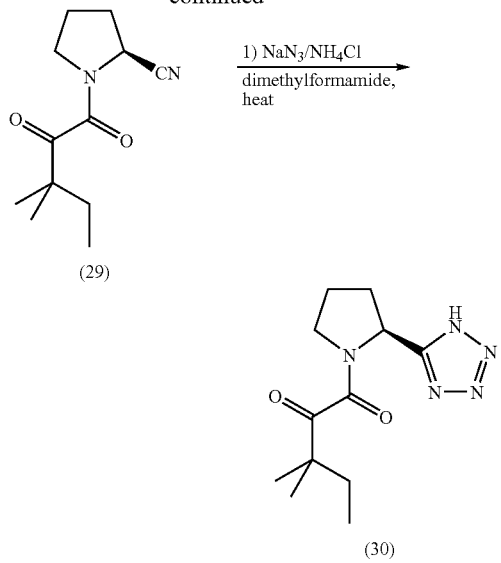

(29)

(30)

Example 2

Synthesis of (2S)-1-(1,2-dioxo-3,3-dimethylpentyl)-2-pyrrolidinecarboxamide. (Compound 34)

Isobutyl chloroformate (20 mmol, 2.7 mL) was added to a solution containing (2S)-1-(1,2-dioxo-3,3-dimethylpentyl)-2-pyrrolidinecarboxylic acid (4.89 g, 20 mmol) (from Example 1) in 50 mL methylene chloride at −10° C. with stirring. After 5 minutes, ammonia was added dropwise (20 mmol, 10 mL of 2 M ethyl alcohol solution). The reaction was warmed up to room temperature after stirring at −10° C. for 30 minutes. The mixture was diluted with water, and extracted into 200 mL methylene chloride. The organic extract was concentrated and further purified by silica gel to give 4.0 g of product as a white solid (81.8% yield). $^1$H NMR (CDCl$_3$): δ0.91 (t, 3H, J=7.5); 1.28 (s, 6H, each); 1.63–1.84 (m, 2H); 1.95–2.22 (m, 3H); 2.46 (m, 1H); 3.55–3.67 (m, 2H); 4.67 (t, 1H, J=7.8); 5.51–5.53 (br, 1H, NH); 6.80 (br, 1H, NH).

Example 3

Synthesis of (2S)-1-(1,2-dioxo-3,3-dimethylpentyl)-2-pyrrolidinecarbonitrile. (Compound 29)

To a solution of 0.465 mL DMF (6 mmol) in 10 mL acetonitrile at 0° C. was added 0.48 mL (5.5 mmol) of oxalyl chloride. A white precipitate formed immediately and was accompanied by gas evolution. When complete, a solution of 1.2 g (5 mmol) of (2S)-1-(1,2-dioxo-3,3-dimethylpentyl)-2-pyrrolidinecarboxamide (from Example 2) in 2.5 mL acetonitrile was added. When the mixture became homogeneous, 0.9 mL (11 mmol) pyridine was added. After 5 min., the mixture was diluted into water and extracted by 200 mL ethyl acetate. The organic layer was concentrated and further purified by silica gel to give 0.8 g product as a white solid (72% yield). $^1$H NMR (CDCl$_3$): δ 0.87 (t, 0.3H, J=7.5); 1.22 (s, 3H); 1.24 (s, 3H); 1.80 (m, 2H); 2.03–2.23 (m, 4H); 3.55 (m, 2H); 4.73 (m, 1H).

Example 4

Synthesis of (2S)-1-(1,2-dioxo-3,3-dimethylpentyl)-2-pyrrolidinetetrazole. (Compound 30)

A mixture of (2S)-1-(1,2-dioxo-3,3-dimethylpentyl)-2-pyrrolidinecarbonitrile (222 mg, 1 mmol)(from Example 3), $NaN_3$ (81 mg, 1.3 mmol) and $NH_4Cl$ (70 mg, 1.3 mmol) in 3 mL DMF was stirred at 130° C. for 16 hours. The mixture was concentrated and purified by silica gel to afford 200 mg product as white solid (75.5% yield). $^1H$ NMR ($CDCl_3$): δ 0.88 (t, 3H, J=7.5); 1.22 (s, 6H); 1.68 (m, 2H); 2.05–2.36 (m, 3H); 2.85 (m, 1H); 3.54 (m, 1H); 3.75 (m, 1H); 5.40 (m, 1H).

The invention being thus described, it will be obvious that the same may be varied in many ways. Such variations are not to be regarded as a departure from the spirit and scope of the invention and all such modification are intended to be included within the scope of the following claims.

Example 5

Synthesis of 3-phenyl-1-propyl (2S)-1-(3,3-dimethyl-1,2-dioxopentyl)-2-pyrrolidinecarboxylate (1)

Methyl (2S)-1-(1,2-dioxo-2-methoxyethyl)-2-pyrrolidinecarboxylate

A solution of L-proline methyl ester hydrochloride (3.08 g; 18.60 mmol) in dry methylene chloride was cooled to 0° C. and treated with triethylamine (3.92 g; 38.74 mmol; 2.1 eq). After stirring the formed slurry under a nitrogen atmosphere for 15 min, a solution of methyl oxalyl chloride (3.20 g; 26.12 mmol) in methylene chloride (45 ml) was added dropwise. The resulting mixture was stirred at 0° C. for 1.5 hour. After filtering to remove solids, the organic phase was washed with water, dried over $MgSO_4$ and concentrated. The crude residue was purified on a silica gel column, eluting with 50% ethyl acetate in hexane, to obtain 3.52 g (88%) of the product as a reddish oil. Mixture of cis-trans amide rotamers; data for trans rotamer given. $^1H$ NMR ($CDCl_3$): d 1.93 (dm, 2H); 2.17 (m, 2H); 3.62 (m, 2H); 3.71 (S, 3H); 3.79, 3.84 (s, 3H total); 4.86 (dd, 1H, J=8.4, 3.3).

Methyl (2S)-1-(1,2-dioxo-3,3-dimethylpentyl)-2-pyrrolidinecarboxylate

A solution of methyl (2S)-1-(1,2-dioxo-2-methoxyethyl)-2-pyrrolidinecarboxylate (2.35 g; 10.90 mmol) in 30 ml of tetrahydrofuran (THF) was cooled to −78° C. and treated with 14.2 ml of a 1.0 M solution of 1,1-dimethylpropyl-magnesium chloride in THF. After stirring the resulting homogeneous mixture at −78° C. for three hours, the mixture was poured into saturated ammonium chloride (100 ml) and extracted into ethyl acetate. The organic phase was washed with water, dried, and concentrated, and the crude material obtained upon removal of the solvent was purified on a silica gel column, eluting with 25% ethyl acetate in hexane, to obtain 2.10 g (75%) of the oxamate as a colorless oil. $^1H$ NMR ($CDCl_3$): d 0.88 (t, 3H); 1.22, 1.26 (s, 3H each); 1.75 (dm, 2H); 1.87–2.10 (m, 3H); 2.23 (m, 1H); 3.54 (m, 2H); 3.76 (s, 3H); 4.52 (dm, 1H, J8.4, 3.4).

Synthesis of (2S)-1-(1,2-dioxo-3,3-dimethylpentyl)-2-pyrrolidinecarboxylic acid A mixture of methyl (2S)-1-(1,2-dioxo-3,3-dimethylpentyl)-2-pyrrolidinecarboxylate (2.10 g; 8.23 mmol), 1 N LiOH (15 ml), and methanol (50 ml) was stirred at 0° C. for 30 minutes and at room temperature overnight. The mixture was acidified to pH 1 with 1 N HCl, diluted with water, and extracted into 100 ml of methylene chloride. The organic extract was washed with brine and concentrated to deliver 1.73 g (87%) of snow-white solid which did not require further purification. $^1H$ NMR ($CDCl_3$): d 0.87 (t, 3H); 1.22, 1.25 (s, 3H each); 1.77 (dm, 2H); 2.02 (m, 2H); 2.17 (m, 1H); 2.25 (m, 1H); 3.53 (dd, 2H, J=10.4, 7.3); 4.55 (dd, 1H, J=8.6, 4.1).

3-Phenyl-1-propyl (2S)-1-(3,3-dimethyl-1,2-dioxopentyl)-2-pyrrolidinecarboxylate (1)

A mixture of (2S)-1-(1,2-dioxo-3,3-dimethylpentyl)-2-pyrrolidine-carboxylic acid (600 mg; 2.49 mmol), 3-phenyl-1-propanol (508 mg; 3.73 mmol), dicyclohexylcarbodiimide (822 mg; 3.98 mmol), camphorsulfonic acid (190 mg; 0.8 mmol) and 4-dimethylaminopyridine (100 mg; 0.8 mmol) in methylene chloride (20 ml) was stirred overnight under a nitrogen atmosphere. The reaction mixture was filtered through Celite to remove solids and concentrated in vacuo, and the crude material was purified on a flash column (25% ethyl acetate in hexane) to obtain 720 mg (80%) of Example 1 as a colorless oil. $^1H$ NMR ($CDCl_3$): d 0.84 (t, 3H); 1.19 (s, 3H); 1.23 (s, 3H); 1.70 (dm, 2H); 1.98 (m, 5H); 2.22 (m, 1H); 2.64 (m, 2H); 3.47 (m, 2H); 4.14 (m, 2H); 4.51 (d, 1H); 7.16 (m, 3H); 7.26 (m, 2H).

FIG. 1. GPI 1046 Protects Retinal Ganglion Cells Against Degeneration Following Retinal Ischemia.

Retinal ganglion cells were retrogradely labeled in adult rats by bilateral injection of fluorogold in their lateral geniculate nuclei. Labeled ganglion cells in the normal rat retina appear as white profiles against the dark background (FIG. 1A). Complete retinal ischemia was produced by infusing normal saline solution into the retinal vitreous cavity of each eye until the intraocular pressure exceeded arterial blood pressure. 28 days after the ischemic episode extensive degeneration of retinal ganglion cell was evidenced by massive reduction in the density of fluorogold labeled cells (FIG. 1B). Administration of GPI 1046 (10 mg/kg, s.c.) 1 hour prior to the ischemic episode and at 10 mg/kg/day for the next four days produced noticeable protection of a large proportion of the vulnerable ganglion cell population (FIG. 1C).

FIG. 2. GPI 1046 Prevents Degeneration of Optic Nerve Axons and Myelin Following Retinal Ischemia Examination of the optic nerves from the same retinal ischemia cases reveals that GPI 1046 produces dramatic protection of optic nerve element from ischemic degeneration. Toluidine blue staining of epon embedded optic nerve cross sections revealed the detail of myelin sheaths (white circles) and optic nerve axons (black centers) in the normal rat optic nerve. Optic nerves from vehicle treated cases examined 28 days after a 1 hour retinal ischemic episode are characterized by a decreased density of optic nerve axons and the appearance of numerous degenerating myelin figures (bright white filled circles). Treatment with GPI 1046 protected the majority of optic nerve axons from degeneration and also dramatically decreased the density of degenerating myelin figures.

FIG. 3. GPI 1046 Provides Moderate Protection Against Retinal Ganglion Cell Death After Optic Nerve Transection Complete transection of the optic nerve 5 mm from the eyeball produces massive degeneration of retinal ganglion cells, representing loss of >87% of the normal ganglion cell population 90 days after the injury (Table 1). Few spared fluorogold pre labeled ganglion cells are present in vehicle treated cases (large white figures) among a population of small microglia that digest the debris of the degenerating cells and take up the fluorogold label (FIG. 3A). Treatment with GPI 1046 for 14 days resulted in a small but not significant increase in the density of retinal ganglion cells that survived 90 days after transection (Table 1) but treatment with GPI 1046 for the first 28 days after transection produced moderate but significant protection of 12.6% of the vulnerable ganglion cell population (Table 1, FIG. 3B).

FIG. 4. GPI 1046 treatment duration significantly affects the process of optic nerve axonal degeneration after transection.

Examination of optic nerve axon density in the proximal stump of the optic nerve from the same cases revealed a more dramatic protection afforded by GPI 1046 treatment. 90 days after transection few ganglion cell axons remain within the optic nerve (FIG. 4B), representing only 5.6% of the normal population. The loss of axons reflects both the death of retinal ganglion cells and the regression or "dying back" of the axons of ~70% of the small surviving ganglion cell population into the retina itself (Table 1). Treatment with GPI 1046 for the first 14 days after optic nerve transection produced a small but significant 5.3% protection of optic nerve axons (FIG. 4D, Table 1), but treatment with the same dose of GPI 1046 for 28 days resulted in the protection of optic nerve axons for the vast majority (81.4%) of spared retinal ganglion cells (FIG. 4C, Table 1).

FIG. 5. GPI 1046 Treatment Produces a Greater Effect on Optic Nerve Axons than Ganglion Cell Bodies This summary figure shows data from FIG. 3 ganglion cell protection and higher power photomicrographs of optic nerve axon protection (FIGS. 5A&B, upper panels). 28 day treatment with GPI 1046 produced a significant increase in the density of large, and particularly medium and small caliber optic nerve axons (FIGS. 5C&D, lower panels).

FIG. 6. GPI 1046 Treatment for 28 Days After Optic Nerve Transection Prevents Myelin Degeneration in the Proximal Stump Myelin basic protein immunohistochemistry labels fascicles (darker labeled 'islands') of myelinated axons in the normal optic nerve (FIG. 6A, upper left). 90 days after transection extensive degeneration of myelin is evident in vehicle treated cases, characterized by the loss of fascicular organization and the appearance of numerous large dense degenerating myelin figures (FIG. 6B, upper right). Treatment with GPI 1046 for the first 14 days after optic nerve transection did not alter the pattern of myelin degeneration (FIG. 6C, lower left panel), and yielded an insignificant 1.6% quantitative recovery in myelin density (Table 1). Extending the GPI 1046 treatment course through the first 28 days after optic nerve transection produced a dramatic preservation of the fascicular staining pattern for myelin basic protein in the proximal stump of the optic nerve and decreased the density of degenerating myelin figures (FIG. 6D, lower right panel), representing a 70% recovery of myelin density (Table 1).

Figure 7:
FIG. 7 shows that FKBP-12 immunohistochemistry labels oligodendroglia (large dark cells with fibrous processes), the cells which produce myelin, located between the fascicles of optic nerve fibers, and also some optic nerve axons.

FIG. 7. FKBP-12 Immunohistochemistry Labels Oligodendroglia (Large Dark Cells with Fibrous Processes), the Cells which Produce Myelin, Located Between the Fascicles of Optic Nerve Fibers, and also Some Optic Nerve Axons.

FIG. 8. GPI 1046 Treatment for 28 Days after Optic Nerve Transection Prevents Myelin Degeneration in the Distal Stump.

Complete transection of the optic nerve leads to degeneration of the distal segments (axon fragments disconnected from the ganglion cell bodies), and the degeneration of their myelin sheaths. 90 days after transection (FIG. 8B) myelin basic protein immunohistochemistry reveals the near total loss of fascicular organization (present in the normal optic nerve, FIG. 8A) and the presence of numerous dense degenerating myelin figures. Quantitation reveals that the cross sectional area of the transected distal stump shrinks by 31% and loses approximately ½ of its myelin (Table 1). Treatment with GPI 1046 for the first 14 days after transection did not protect against shrinkage of the distal stump but did slightly increase the density of myelin, though the density of degenerating myelin figures remained high (FIG. 8C, Table 1). GPI 1046 treatment through the first 28 days produced dramatic protection of the fascicular pattern of myelin labeling, decreased the density of degenerating myelin figures, prevented cross sectional shrinkage of the distal stump of the transected nerve and maintained the myelin levels at ~99% of normal levels (FIG. 8D, Table 1).

FIG. 9. 28 Day Treatment with GPI 1046 Treatment Beginning 8 Weeks after Onset of Streptozotocin Induced Diabetes Decreases the Extent of Neovascularization in The Inner and Outer Retina and Protects Neurons in the Inner Nuclear Layer (INL) and Ganglion Cell Layer (GCL) From Degeneration.

Negative images of cresyl violet stained tangential retinal sections reveals perikarya in the three cellular layers (FIG. 9A). The retinae of streptozotocin treated animals administered only vehicle FIG. 9B) exhibited loss of cells from the ONL and INL, decreased thickness of the Outer plexiform layer (the dark area between ONL and INL) and a dramatic increase in the size and density of retinal blood vessels (large black circular outlines) in the INL, OPL, ONL and the photoreceptor layer (PR, the gray fuzzy area above the ONL). GPI 1046 treatment reduced neovascularization (i.e. prevented the proliferation of blood vessels) in the PR, ONL, OPL and INL. Although GPI 1046 did not appear to protect against neuronal loss in the ONL, it appeared to decrease the loss of neurons in both the INL and GCL compared to streptozotocin/vehicle treated controls.

Example 6

In Vivo Retinal Ganglion Cell and Optic Nerve Axon Tests

The extent of degeneration reduction or prevention in retinal ganglion cells and optic nerve axons was determined in a vision loss model utilizing surgical optic nerve transection to simulate mechanical damage to the optic nerve. The effects of several neuroimmunophilin FKBP ligands on retinal ganglion cells neuroprotection and optic nerve axon density was determined experimentally, comparing 14 day and 28 day neuroimmunophilin FKBP ligand treatments. The effects of treatment with neuroimmunophilin FKBP ligands on retinal ganglion cells and optic nerve axons was correlated.

Surgical Procedures

Adult male Sprague Dawley rats (3 months old, 225–250 grams) were anesthetized with a ketamine (87 mg/kg) and xylazine (13 mg/kg) mixture. Retinal ganglion cells were pre-labeled by bilateral stereotaxic injection of the fluorescent retrogradely transported marker fluoro-gold (FG, 0.5 microliters of 2.5% solution in saline) at the coordinates of the LGNd (4.5 millimeters post β3,5 millimeters lateral, 4.6 millimeters below dura). Four days later, FG labeled rats underwent a second surgery for microsurgical bilateral intraorbital optic nerve transection 4–5 millimeters behind the orbit.

Experimental animals were divided into six experimental groups of six rats (12 eyes) per group. One group received a neuroimmunophilin FKBP ligand (10 milligrams per kg per day sc in PEG vehicle (20 percent propylene glycol, 20 percent ethanol, and 60 percent saline)) for 14 days. A second group received the same neuroimmunophilin FKBP ligand dose for 28 days. Each treated group had a corresponding sham/surgery and transection control group which received corresponding 14 or 28 day dosing with the vehicle only.

All animals were sacrificed 90 days after optic nerve transection and perfused pericardially with formalin. All eyes and optic nerves stumps were removed. Cases were excluded from the study if the optic nerve vasculature was damaged or if FG labeling was absent in the retina.

Retinal Ganglion Cell Counts

Retinas were removed from eyes and prepared for whole-mount analysis. For each group, five eyes with dense and intense FG labeling were selected for quantitative analysis using a 20 power objective. Digital images were obtained from five fields in the central retina (3–4 millimeters radial to optic nerve head). FG labeled Large (>18 μm), medium (12–16 μm), and small (<10 μm) ganglion cells and microglia were counted in five 400 μm by 400 μm fields per case, 5 cases per group.

Examination of Optic Nerves

Proximal and distal optic nerve stumps were identified, measured, and transferred to 30% sucrose saline. The proximal stumps of five nerves were blocked and affixed to a chuck, and 10 micron cross sections were cut on a cryostat; one in ten sections were saved per set. Sections including the region 1–2 mm behind the orbit were reacted for RT97 neurofilament immunohistochemistry. Analysis of optic nerve axon density was performed using a 63 power oil immersion lens, a Dage 81 camera, and the Simple Image Analysis program. RT97 positive optic nerve axons were counted in three 200 μm by 200 μm fields per nerve. The area of the nerve was also determined for each case at 10 power.

As depicted graphically in Table I&II, the 14 day course of treatment with a neuroimmunophilin FKBP ligand provided moderate neuroprotection of retinal ganglion cells observed 28 days after optic nerve transection. However, by 90 days after transection, only 5% of the ganglion cell population remained viable.

90 days after optic nerve transection the number of axons persisting in the proximal stump of the optic nerve represented approximately one half of the number of surviving ganglion cells in groups of animals that received vehicle alone or the 14 day course of treatment with a neuroimmunophilin FKBP ligand. These results indicate that over half of the transected ganglion cell axons retract beyond the optic nerve head, and that treatment with a neuroimmunophilin FKBP ligand during the first 14 days after optic nerve transection is not sufficient to arrest this retraction.

As depicted graphically in Table I&II, more prolonged treatment with a neuroimmunophilin FKBP ligand during the 28 day course of treatment produced a moderate increase in retinal ganglion cell neuroprotection. Approximately 12% of the vulnerable retinal ganglion cell population was protected. A

TABLE I

Effect of prolonged GPI 1046 treatment on retinal ganglion cell survival, optic nerve axon perservation, and myelination 90 days after optic nerve transection

| GROUP | RGC Counts[1] | ON Axon density[2] | ON head area (% sham) | % RGCs Rescued | increased ON axon density[3] | Spared RGC population | ON axon Count[4] | % surviving RGCs with ON axons | Proximal optic nerve myelin basic protein Density[5] | Distal optic nerve myelin basic protein Density[6] |
|---|---|---|---|---|---|---|---|---|---|---|
| Sham | 290 ± 14.8 | 7600* | 100% | — | | 120,000* | 120,000 | 100% | normal | |
| ONT/ Vehicle | 35.9 ± 2.8 | 428 ± 34 | 68% | (87% loss) | | 14,855 | 4593 | 30.9% | 52 + 5.2 SEM % loss | 31% shrinkage 52.3% loss |
| ONT/ 14 Days GPI 1046 | 49 ± 5.3 | 569 ± 23 | 76% | 5.3% | 1.5X | 20,275 | 6820 | 33.6% | 1.6 ± 3.0 SEM % recovery | 33% shrinkage 47% loss |
| ONT/ 28 days GPI 1046 | 67.9 ± 5.8* | 1526 ± 120* | 95%* | 12.6%* | 5.0X | 28,096* | 22,861* | 81.4% | 70 ± 6.3 SEM % recovery* | 56% less shrinkage* 99% myelin preservation* |

*significance p < .001
[1]Mean density + SEM of Fluoro-gold labeled retinal ganglion cells (RGC) in 400 μm × 400 μm sample gridfields.
[2]mean density + SEM of RT97 neurofilament antibody labeled optic nerve (ON) axons in 200 μm × 200 μm region of interest
*estimate for 200 μm × 200 μm region in normal optic nerve assuming 120,000 RGC axons in normal rat optic nerve, measured to be 0.630 mm$^2$ mean cross sectional area
[3]adjusted for optic nerve diameter
[4]calculated by multiplying axonal density by ON area
[5]determined from 20X analysis of % areal coverage of optic nerve cross section
[6]shrinkage determined by comparing cross sectional area to sham control, myelin leves determined by multiplying cross sectional area by myelin density

TABLE II

Neuroprotective effect of GPI 1046 on retinal ganglion cells following optic nerve transection

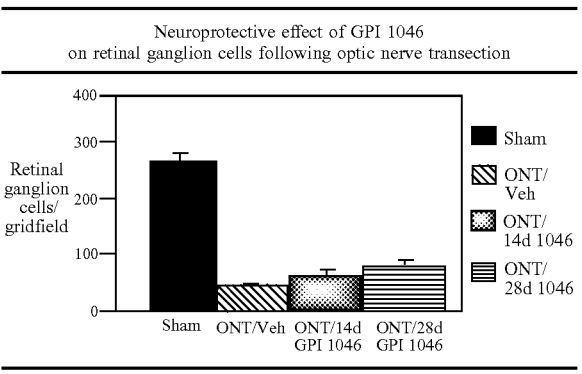

similar proportion (~50%) of optic nerve axon density sparing was also observed. These results demonstrate the startling result that extending the duration of treatment with a neuroimmunophilin FKBP ligands to 28 days after transection completely arrests the regression of damaged axons for essentially the entire surviving population of retinal ganglion cells.

Additional results are set forth in Tables III & IV.

TABLE III

Correlation between Retinal Ganglion Cell and Optic Nerve Axon Sparing at 90 days following optic nerve transection and 14 or 28 day GPI 1046 treatment

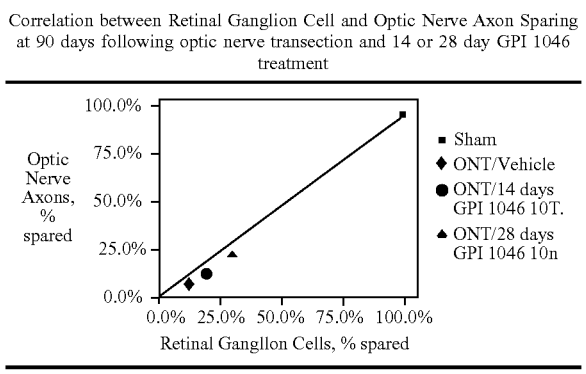

TABLE IV

GPI 1046 preserves optic nerve axons in the proximal stump following transection

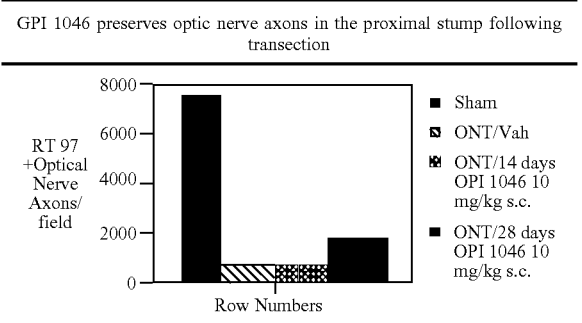

Example 7

A patient is suffering from macular degeneration. A derivative as identified above, alone or in combination with one or more other neopsic factors, or a pharmaceutical composition comprising the same, may be administered to the patient. A reduction in vision loss, prevention of vision degeneration, and/or promotion of vision regeneration are is expected to occur following treatment.

Example 8

A patient is suffering from glaucoma, resulting in cupping of the optic nerve disc and damage to nerve fibers. A derivative as identified above, alone or in combination with one or more other neopsic factors, or a pharmaceutical composition comprising the same, may be administered to the patient. A reduction in vision loss, prevention of vision degeneration, and/or promotion of vision regeneration are/is expected to occur following treatment.

Example 9

A patient is suffering from cataracts requiring surgery. Following surgery, a derivative as identified above, alone or in combination with one or more other neopsic factors, or a pharmaceutical composition comprising the same, may be administered to the patient. A reduction in vision loss, prevention of vision degeneration, and/or promotion of vision regeneration are/is expected to occur following treatment.

Example 10

A patient is suffering from an impairment or blockage of retinal blood supply relating to diabetic retinopathy, ischemic optic neuropathy, or retinal artery or vein blockage. A derivative as identified above, alone or in combination with one or more other neopsic factors, or a pharmaceutical composition comprising the same, may be administered to the patient. A reduction in vision loss, prevention of vision degeneration, and/or promotion of vision regeneration are/is expected to occur following treatment.

Example 11

A patient is suffering from a detached retina. A derivative as identified above, alone or in combination with one or more other neopsic factors, or a pharmaceutical composition comprising the same, may be administered to the patient. A reduction in vision loss, prevention of vision degeneration, and/or promotion of vision regeneration are/is expected to occur following treatment.

Example 12

A patient is suffering from tissue damage caused by inflammation associated with uveitis or conjunctivitis. A derivative as identified above, alone or in combination with one or more other neopsic factors, or a pharmaceutical composition comprising the same, may be administered to the patient. A reduction in vision loss, prevention of vision degeneration, and/or promotion of vision regeneration are/is expected to occur following treatment.

Example 13

A patient is suffering from photoreceptor damage caused by chronic or acute exposure to ultraviolet light. A derivative as identified above, alone or in combination with one or more other neopsic factors, or a pharmaceutical composition comprising the same, may be administered to the patient. A reduction in vision loss, prevention of vision degeneration, and/or promotion of vision regeneration are/is expected to occur following treatment.

Example 14

A patient is suffering from optic neuritis. A derivative as identified above, alone or in combination with one or more other neopsic factors, or a pharmaceutical composition comprising the same, may be administered to the patient. A reduction in vision loss, prevention of vision degeneration, and/or promotion of vision regeneration are/is expected to occur following treatment.

Example 15

A patient is suffering from tissue damage associated with a "dry eye" disorder. A derivative as identified above, alone or in combination with one or more other neopsic factors, or a pnarmaceutical composition comprising the same, may be administered to the patient. A reduction in vision loss, prevention of vision degeneration, and/or promotion of vision regeneration are/is expected to occur following treatment.

Example 16

Efficacy of Representative Compounds from Different Immunophilin Ligand Series in Protecting Retinal Ganglion Cell Axons from Degeneration Following Optic Nerve Transection is Set Forth in Table V Efficacy of Representative Compounds from Different Immunophilin Ligand Series in Protecting Retinal Ganglion Cell Axons from Degeneration Following Optic Nerve Transection

TABLE V

| Compound | Structure | Comments | RT97 + RGC axon density 14 days after ON transection (% ON axons rescued) |
|---|---|---|---|
| B | 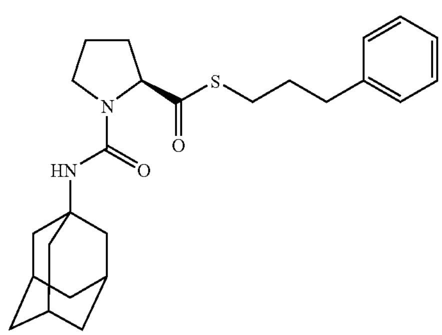 | Adamantl Thioester of urea Ki rotomase = 149 nM Clearance = ? μl/min | 100.0% ± 5.2% SEM |
| A GPI 1046 | | Ester Ki rotomase = 7.5 nM Clearance = 63.5 μl/min | 60.5% ± 3.9 SEM |
| C | 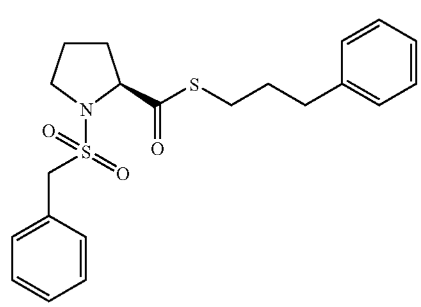 | Sulfonamide Ki rotomase = 107 nM Clearance = 31.1 μl/min | 60.4% ± 3.1% SEM |

TABLE V-continued

| Compound | Structure | Comments | RT97 + RGC axon density 14 days after ON transection (% ON axons rescued) |
|---|---|---|---|
| D | 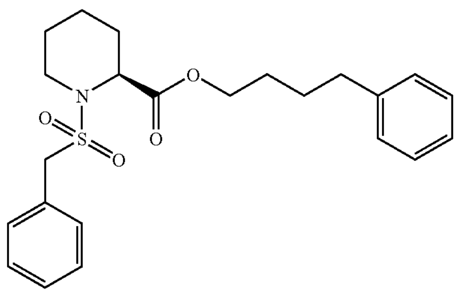 | Pipecolic sulfonamide<br>Ki rotomase = nM<br>Clearance = μl/min | 58.4% ±<br>6.4% SEM |
| E | 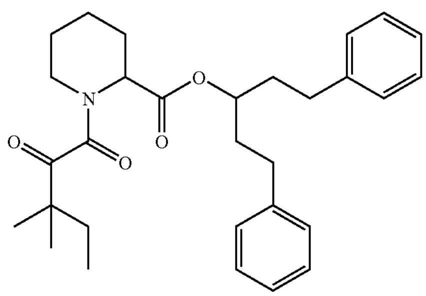 | Ester of pipecolic acid<br>Ki rotomase = 20 nM<br>Clearance = 41.8 μl/ml | 56.6% ±<br>9.4% SEM |
| F | 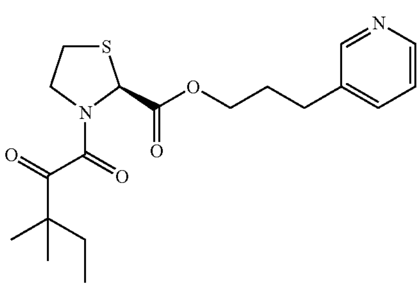 | Proline heterocycle<br>Analog of GPI 1046<br>Ki rotomase = 272 nM<br>Clearance = ? μl/min | 55.1% ±<br>5.9% SEM |
| G | 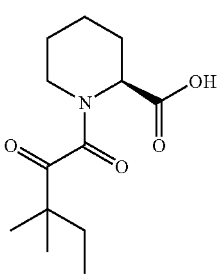 | Pipecolic acid<br>dimethyl ketone<br>Ki rotomase > 10,000 nM<br>Clearance = ? μl/min | 34.0% ±<br>4.8% SEM |
| H | 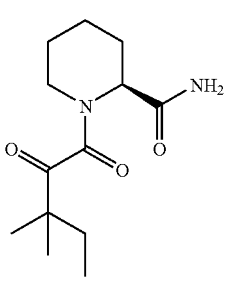 | Ki rotomase = nM<br>Clearance = ? μl/min | 30.3% ±<br>8.0% SEM |

TABLE V-continued

| Compound | Structure | Comments | RT97 + RGC axon density 14 days after ON transection (% ON axons rescued) |
| --- | --- | --- | --- |
| I | 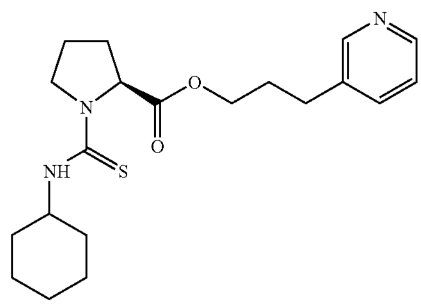 | Ester of Thiourea<br>Ki rotomase = 131 nM<br>Clearance = 8.0 µl/min | 23.8% ± 5.3 SEM |
| J | 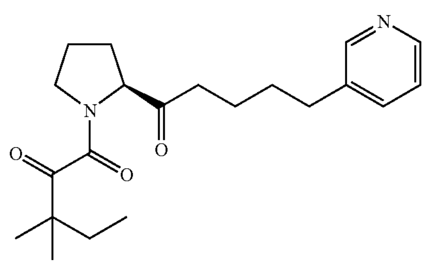 | Ketone<br>analog of GPI 1046<br>Ki rotomase = 210 nM<br>Clearance = 1.5 µl/min | 15.8% ± 4.8% SEM |
| K | 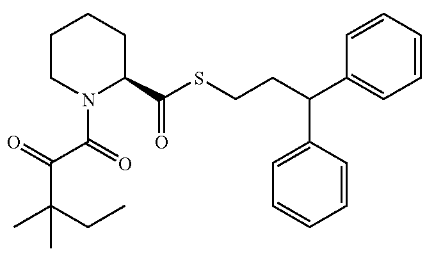 | Pipecolic acid Thioester<br>Ki rotomase = 86 nM<br>Clearance = 4.5 µl/min | 13.0% ± 4.2% SEM |
| L | 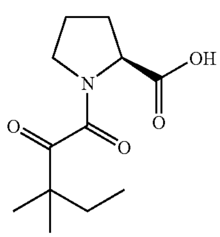 | Prolyl acid<br>Ki rotomase = >7743 nM<br>Clearance = 5.2 µl/min | 7.8% ± 3.0% SEM |
| M | 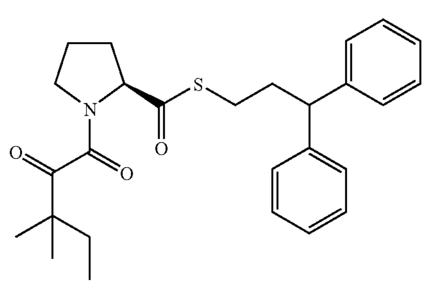 | Thioester<br>Ki rotomase = 7 nM<br>Clearance = 12.5 µl/min | −6.3% ± 3.9% SEM |

TABLE V-continued

| Compound | Structure | Comments | RT97 + RGC axon density 14 days after ON transection (% ON axons rescued) |
|---|---|---|---|
| N | 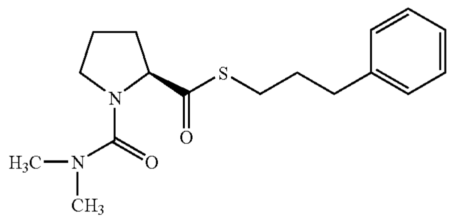 | Ki rotomase = 722 nM<br>Clearance = 21.9 µl/ml | |

Example 17

The FKBP Neuroimmunophilin Ligand GPI-1046 Enhances Retinal Ganglion Cell Survival and Arrests Axonal Dying Back Following Optic Nerve Transection

Transection of the mammalian optic nerve results in a brief period of abortive regeneration, but the majority of axotomized neurons die and the axons from many persisting ganglion cells die back beyond the optic nerve head. The present Example was designed to examine the neuroprotective effects of GPI-1046 following optic nerve transection.

Retinal ganglion cells in adult male Sprague Dawley rats were retrogradely labeled by fluorogold injection in the LGNd and four days later the optic nerves were transected 5 mm behind the globe. Groups of animals received either GPI-1046 10 mg/kg/day s.c. or vehicle for 28 days. All experimental animals and controls were sacrificed 90 days after transection.

By 90 days only—10% of the FG labeled ganglion cell population survived but less than half of these neurons maintained axons that extended past the optic nerve head, as detected with RT97 neurofilament immunohistochemistry GPI-1046 treatment produced a moderate degree of perikaryal neuroprotection, sparing 25% of the ganglion cell population, and preserved the axons of virtually all protected neurons in the proximal stump of the transected nerve. These results indicate that treatment with the FKBP neuroimmunophilin ligand GPI-1046 produces a fundamental alteration in the pathological process following injury to CNS tracts.

These results also demonstrate that the small molecule FKBP neuroimmunophilin ligand GPI 1046 enhances neurite outgrowth in culture, enhance peripheral nerve regeneration, and stimulate sprouting within the CNS following partial deafferentation.

Example 18

Neuroimmunophilin Ligands Promote Recovery from the Peripheral Sensory Neuropathy Associated with Streptozotocin-Induced Diabetes

Peripheral neuropathy is a common debilitating complication of Type 2 diabetes in some 30–40% of diabetic patients. Neurotrophic factors such as nerve growth factor (NGF) are known to promote survival of developing and adult neurons of the peripheral nervous system (PNS), and have also been evaluated as treatments for diabetic peripheral neuropathy. Some of the selective ligands of the neuroimmunophilin FKBP-12 such as the small molecule GPI-1046, have also been shown to promote repair and regeneration in the central and peripheral nervous systems (Proc. Nat'l. Acad. Sci. USA 94, 2019–2024, 1997).

In this Example the potential therapeutic effects of GPI-1046 were evaluated for its ability to improve sensory function in the streptozotocin-induced diabetic rat. The procedure involved using Male Wistar rats which were given a single injection of streptozotocin (65 mg/kg i.v.). Blood glucose levels were determined weekly for the first three weeks and on the last week of the experiment. Animals were evaluated weekly for signs of sensory neuropathy using the conventional hot plate and tail flick apparatus test procedures. After six weeks, treatment either with GPI-1046 or vehicle was initiated.

The results demonstrated that behavioral testing using the hot plate and the tail flick apparatus indicated improvement in latency in lesioned animals treated for 6 weeks with GPI-1046 at 10 mg/kg s.c. The results also showed that GPI-1046 ameliorates the behavioral sequelae of diabetic sensory neuropathy and may offer some relief for patients suffering from diabetic peripheral neuropathy.

Morris Watermaze/Aging and Memory Test Procedure

Aged rodents exhibit marked individual differences in performance on a variety of behavioral tasks, including two-choice spatial discrimination in a modified T-maze, spatial discrimination in a circular platform task, passive avoidance, radial maze tasks, and spatial navigation in a water pool.

In all of these tasks, a proportion of aged rats or mice perform as well as the vast majority of young control animals, while other animals display severe impairments in memory function compared to young animals. For example, Fischer and colleagues showed that the proportion of rats displaying significant impairments in spatial navigation increases with age, (Fischer et al. 1991b) with 8% of all 12 month old, 45% of 18 month old, 53% of 24 month old, and 90% of all 30 month old rats displaying, impairments in spatial acquisition of the Morris watermaze task relative to young controls.

Specifically, rodent spatial learning and memory decline during aging has been accepted by many investigators as an intriguing correlative animal model of human senile dementia. Cholinergic function in the hippocampus has been extensively studied as a component of spatial learning in rodents, and declining hippocampal cholinergic function has been noted in parallel with the development of learning and memory impairments. In addition, other neurotransmitter systems have been shown to contribute to spatial learning, and to decline with age, such as the dopaminergic and noradrenergic, serotonergic, and glutamatergic systems.

Also, reports on age-related deficits of hippocampal long-term potentiation (LTP)-induction, a reduction in theta rhythm frequency, a loss of experience-dependent plasticity of hippocampal place-units, and reductions in hippocampal protein kinase C are in keeping with the concept that no single underlying pathology can be identified as the cause of age-related behavioral impairment in rodents. However, the various experimental therapeutic approaches that have been undertaken to improve memory function in aged rodents have been somewhat slanted towards the cholinergic hypothesis.

The Morris watermaze is widely used for assessing spatial memory formation and retention in experimental animals. The test depends on the animal's ability to utilize spatial visual information in order to locate a submerged escape platform in a water tank. It is important that the tank itself be as devoid of specific visual features as possible—thus, it is always circular in shape, the sides are kept smooth and in uniform dull colors and the water is rendered opaque with nontoxic watercolor pigment or powdered milk. This is to ensure that the animal navigates only by the use of more distant visual cues, or by the use of intra-maze cues specifically provided by the experimenter.

The tank is filled to a level which forces the animal to swim actively. Normal mice and rats react aversively to the swimming part of the test and will climb onto, and remain on, an escape platform from which they are removed to a heated resting cage.

If the platform is visible (i.e. above the surface), animals placed in the tank will quickly learn to home in on the platform and climb out onto it. Testing with a visible platform will also ensure that the experimental animals are not blind and show sufficient motivation and stamina to perform the task, which can be important in experiments involving aged rodents. If the platform is invisible (i.e. submerged just below the surface), normal animals learn to use distant visual cues in the test room for orientation in the test tank, and, when placed in the tank, will quickly home in on the approximate location of the platform and circle in that area until the platform is found.

The animals' path, speed, and swim time are tracked with a ceiling camera for later computerized analysis. Over the course of several successive trials, spatial learning can therefore be defined as a drop of distance swum, or time elapsed, from placement in the tank until escape onto the invisible platform.

The test can be adapted to assess several aspects of spatial memory: a) acquisition of a cued task, where the animal's ability to link one visual cue directly with the escape platform depends on cortical function (i.e. a ball is suspended over the escape platform and the animal learns to follow this cue to find the platform); b) acquisition of a spatial task, where the animal's ability to learn the location of a submerged escape platform based on a combination of distant visual cues is dependent upon hippocampal function (i.e. the animal learns to triangulate its position in the tank by visually aligning the paper-tower dispenser with the door and ceiling lamp); c) retention of a successfully acquired spatial task, which is predominantly dependant on cortical function (i.e. the animal must remember the spatial location of the platform over several weeks); d) a hippocampus-dependant reversal task where the animals must reacquire a new spatial platform location (i.e. the platform is moved to a new location between swim trials and the animal must abandon its previous search strategy and acquire a new one).

These different modifications of the Morris watermaze procedure can be applied in sequence to the same set of experimental animals and allow for a thorough characterization of their spatial memory performance and its decline with normal ageing. Moreover, such a series of sequential memory tests sheds some light on the functional integrity of the specific brain systems involved in the acquisition and retention of spatial memory (e.g. rats with cholinergic lesions of the hippocampus may remember a platform location acquired weeks before, but persevere over the old platform location after the platform is moved).

Example 19

Effects of Chronic GPI-1046 Administration on Spatial Learning and Memory in Aged Rodents This Example shows the effects of chronic treatment with the systemically available FKBP-ligand GPI-1046 on spatial learning and memory in aged rodents.

The procedure involved using three-month old (young) and 18–19 month old male C57BL/6N-Nia (aged) mice which habituated to the well known and conventional Morris watermaze during a 4 trials/day, 3–4 day visible platform training phase. Subsequent spatial acquisition testing was conducting as follows: All mice were given 4 trials/day (block), for 5 days. Maximum swim time was 90 seconds. Aged mice were allocated to an "aged impaired" group if their performance during blocks 4 or 5 of the acquisition phase was >1 S.D. above the mean of "young" mice, and to an "aged non-impaired" group if their performance was <0.5 S.D. above the mean of "young" mice. Aged groups were then split into statistically similar "GPI-1046" and "vehicle" groups.

Daily treatment with 10 mg/kg GPI-1046 was initiated 3 days after the end of acquisition training, and continued through retention testing. Retention testing began after 3 weeks of dosing using the same methods as the acquisition phase. Swim Distances (cm) were analyzed in a 7×5 ANOVA including Groups and Blocks (1–5) as factors in the analysis, treating Blocks as a repeated measure.

The results showed that planned contrasts revealed that there were significant differences between the "young", and "raged impaired-vehicle and GPI-1046" treated groups at the end of the acquisition phase, $F_{1,58}=26.75$, P=0.0001, and $F_{1,58}=17.70$, P=0.0001 respectively. While there were no significant differences between the two "aged impaired" groups, $F_{1,58}=0.67$, P=0.42. During retention testing, however, "aged impaired-vehicle" treated animals performed significantly poorer than "aged impaired—GPI-1046", and "young" animals, $F_{1,69}=8.11$, P=0.006, and $F_{1,69}=25.45$, P=0.0001 respectively. There was no longer any statistically significant difference between the "young" and "aged impaired"—GPI-1046" treated groups during the retention phase, $F_{1,69}=3.09$, P=0.08. In summary, systemic treatment with GPI-1046 significantly enhanced spatial memory performance of mice with age-related spatial memory impairments.

The invention being thus described, it will be obvious that the same may be varied in many ways. Such variations are not to be regarded as a departure from the spirit and scope of the invention and all such modification are intended to be included within the scope of the following claims.

What is claimed is:

1. A method for improving naturally-occurring vision in an animal, in the absence of any opthalmologic disorder, disease, or injury or treating a nerve-related vision disorder in a mammal in need thereof, which comprises administering to said mammal an effective amount of an N-heterocyclic ring compound containing a carboxylic acid or carboxylic acid isostere moiety thereof attached to the 2-carbon of the N-heterocyclic ring, wherein the carboxylic acid isostere is selected from the group consisting of:

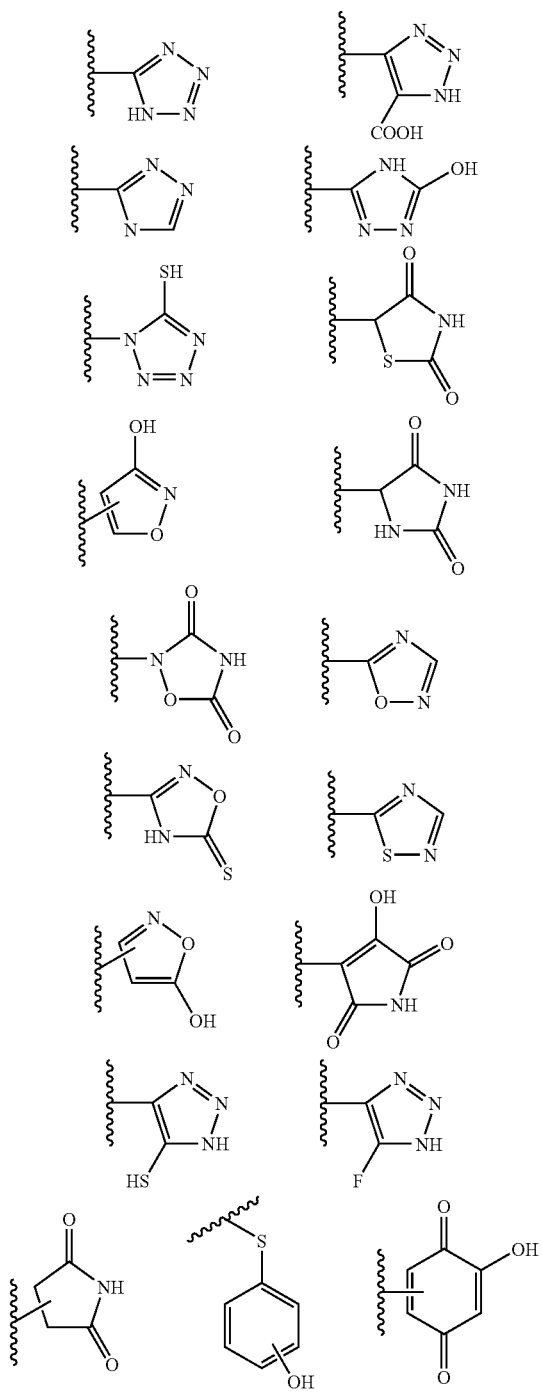

wherein the nerve-related vision disorder is selected from the group consisting of the following:

visual impairments;
orbital disorders;
disorders of the lacrimal apparatus;
disorders of the eyelids;
disorders of the conjunctiva;
disorders of the cornea;
cataract;
disorders of the uveal tract;
disorders of the retina;
disorders of the optic nerve or visual pathways;
free radical induced eye disorders and diseases;
immunologically-mediated eye disorders and diseases;
nerve-related physical injury affecting vision; and
nerve-related symptoms and complications of eye disease, nerve-related symptoms and complications of eye disorders, and nerve-related symptoms and complications of physical injury affecting vision.

2. The method of claim 1, wherein the compound is immunosuppressive.

3. The method of claim 1, wherein the compound has an affinity for an FKBP-type immunophilin.

4. The method of claim 3, wherein the FKBP-type immunophilin is FKBP-12.

5. The method of claim 1, wherein the compound is of formula (I):

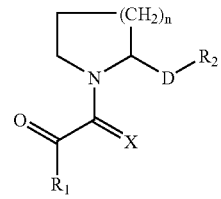

I or a pharmaceutically acceptable salt, ester, or solvate thereof, where n is 1–3;

X is either O or S;

$R_1$ is selected from the group consisting of $C_1$–$C_9$ straight or branched chain alkyl; $C_2$–$C_9$ straight or branched chain alkenyl, aryl, heteroaryl, carbocycle, or heterocycle;

D is a bond, or a $C_1$–$C_{10}$ straight or branched chain alkyl, $C_2$–$C_{10}$ alkenyl or $C_2$–$C_{10}$ alkynyl; and $R_2$ is a carboxylic acid or a carboxylic acid isostere.

6. The method of claim 5, wherein $R_2$ is a carbocycle or hetetocycle containing any combination of $CH_2$, O, S, or N in any chemically stable oxidation state, where any of the atoms of said ring structure are optionally substituted in one or more positions with $R_3$, wherein $R_3$ is hydrogen, hydroxy, halo, haloalkyl, thiocarbonyl, alkoxy, alkenoxy, alkylaryloxy, aryloxy, arylalkyloxy, cyano, nitro, imino, alkylamino, aminoalkyl, suithydryl, thioalkyl, alkylthio, sulfonyl, $C_1$–$C_6$ straight or branched chain alkyl, $C_2$–$C_6$ straight or branched chain alkenyl or alkynyl, aryl, heteroaryl, carbocycle, heterocycle, and $CO_2R^4$ where $R^4$ is hydrogen or $C_1$–$C_9$ straight or branched chain alkyl or alkenyl.

7. The method of claim 5, wherein R₂ is selected from the group below:
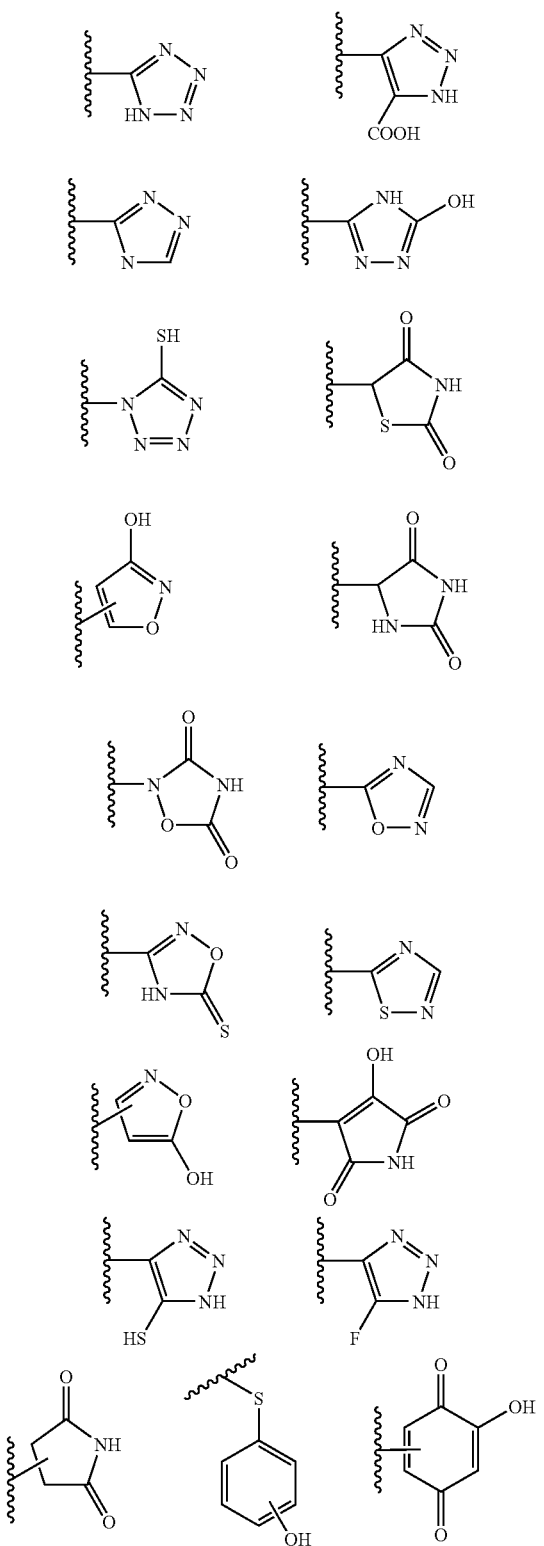
8. The method of claim 5, wherein R₂ is selected from the group consisting of —COOH, —SO₃H, —SO₂HNR³, —PO₂(R³)₂, —CN, —PO₃(R³)₂, —OR³, —SR³, —NH-COR³, —N(R³)₂, —CON(R³)₂, —CONH(O)R³, —CONHNHSO₂R³, —COHNSO₂R³, and —CONR³CN.
9. The method of claim 5, wherein the compound is selected from the group consisting of:
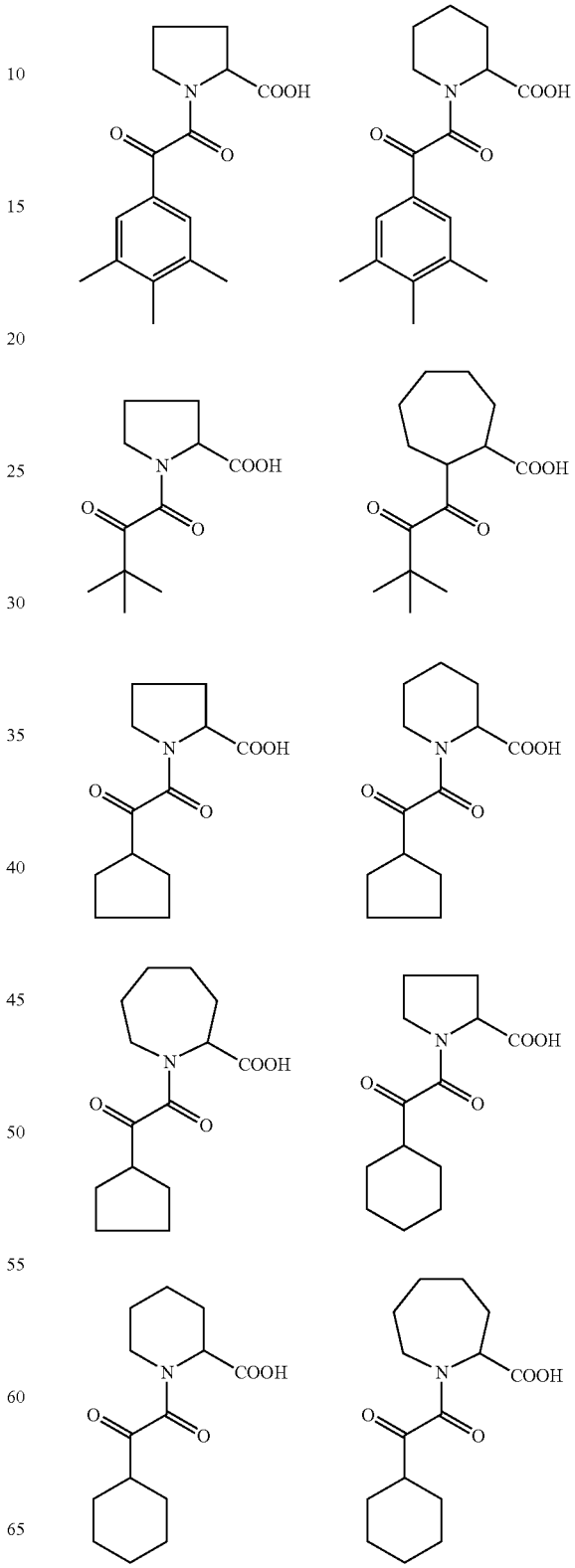

-continued
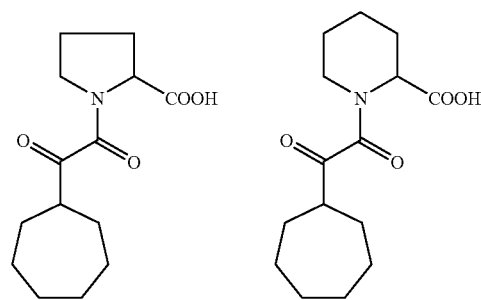
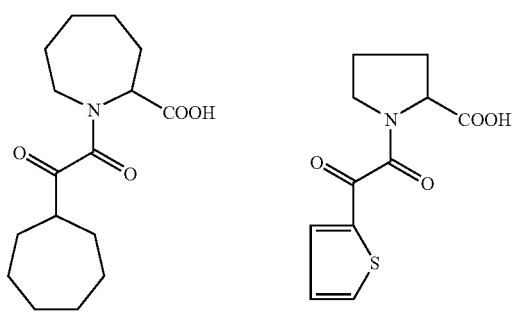
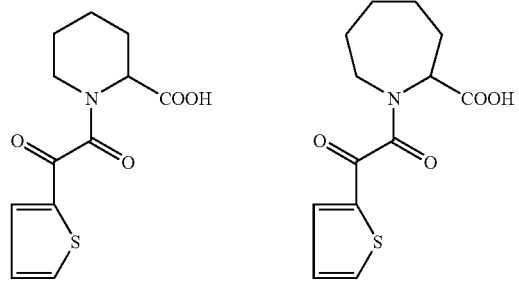
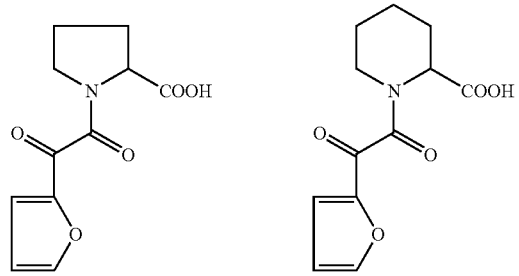
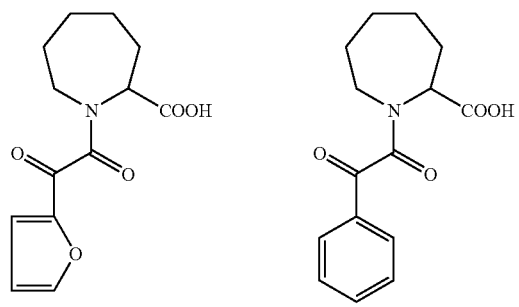
-continued
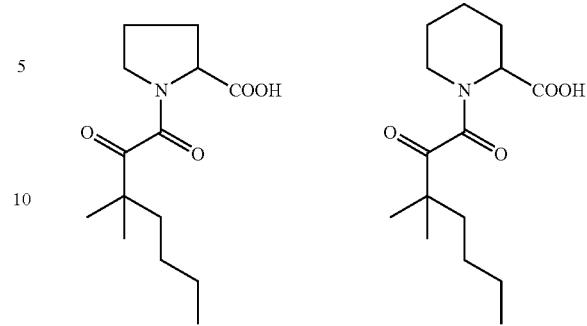
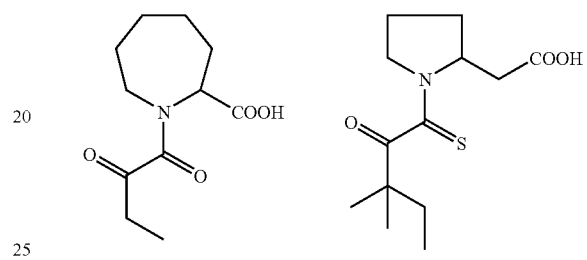
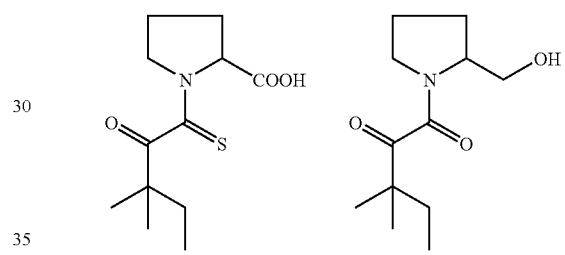
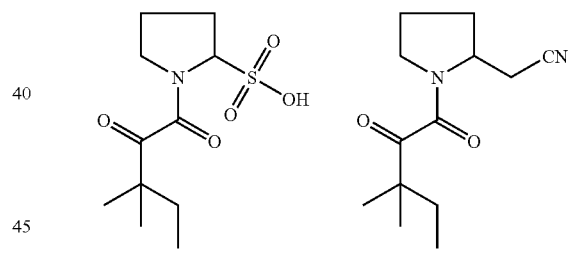
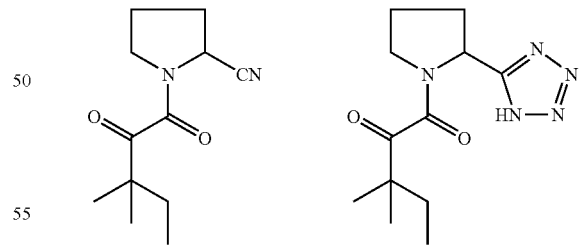
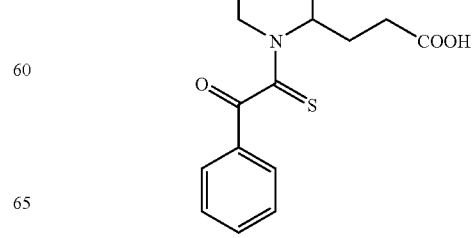

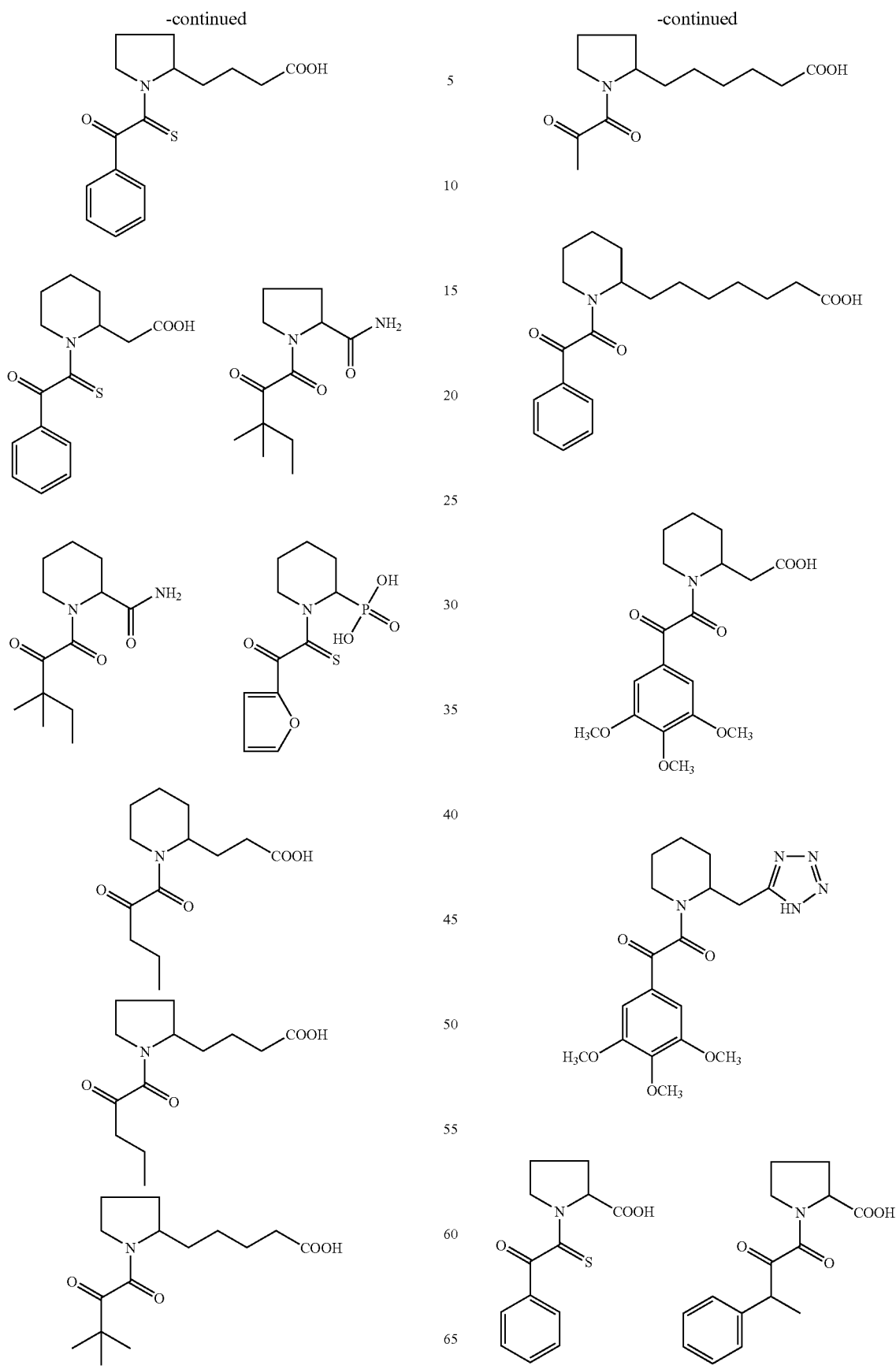

-continued
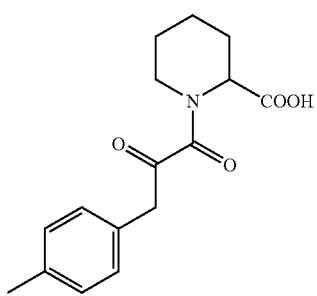
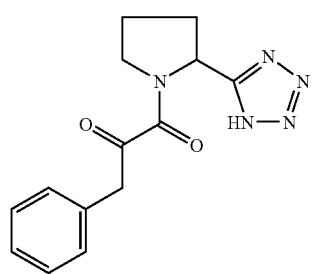
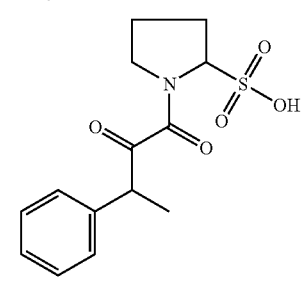
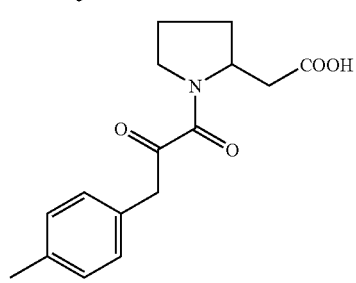
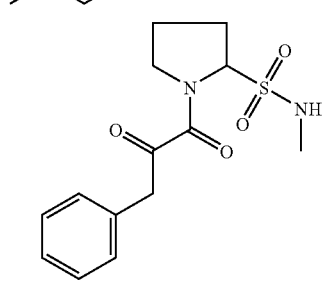
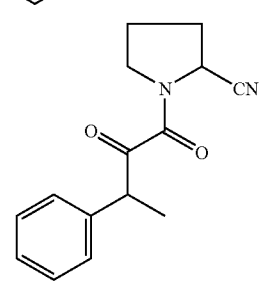
-continued
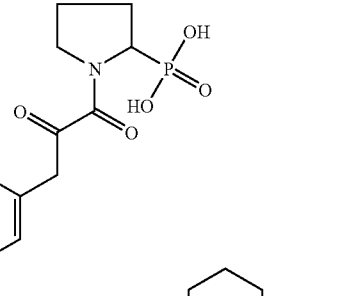
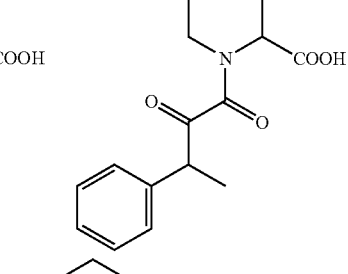
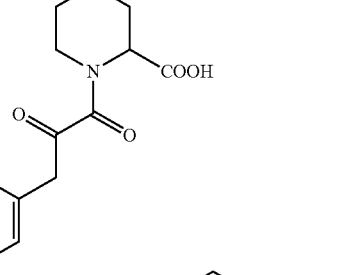
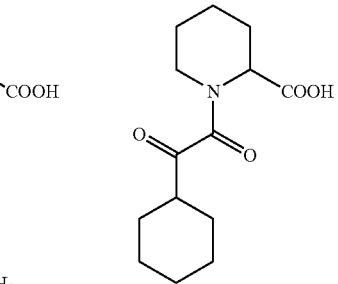
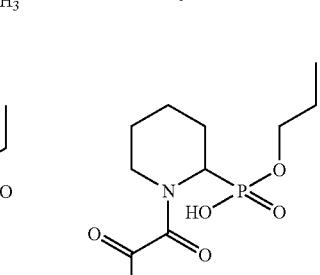
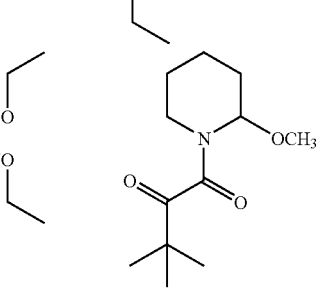

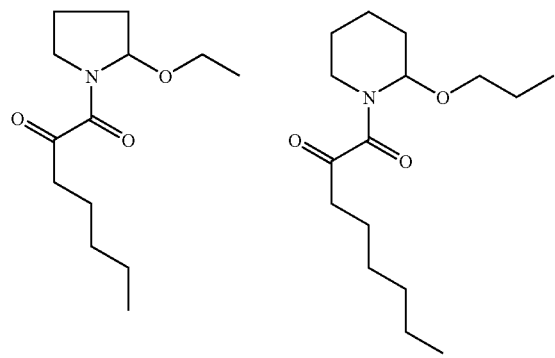
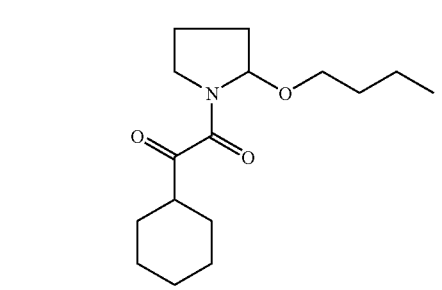
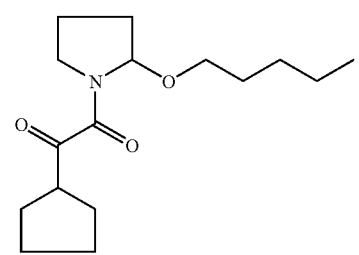
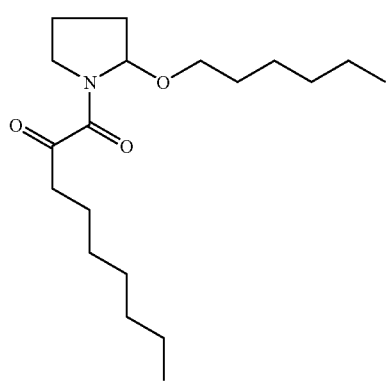
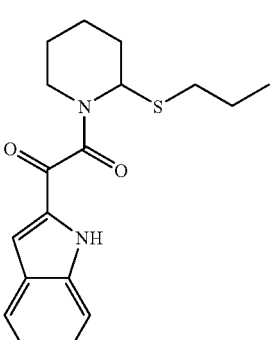
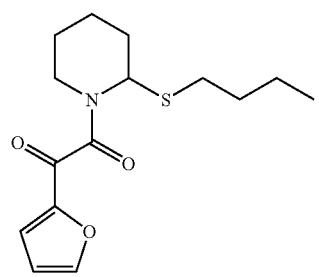
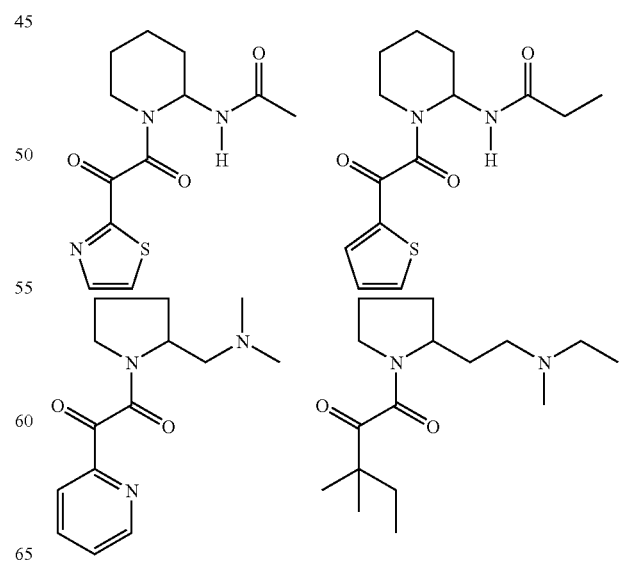

-continued
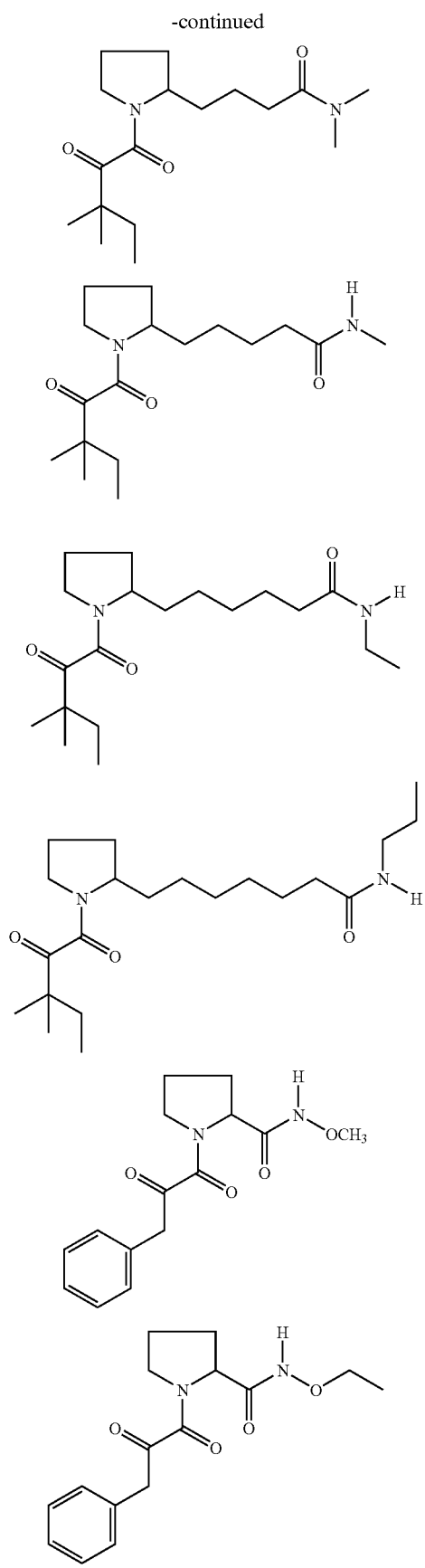
-continued
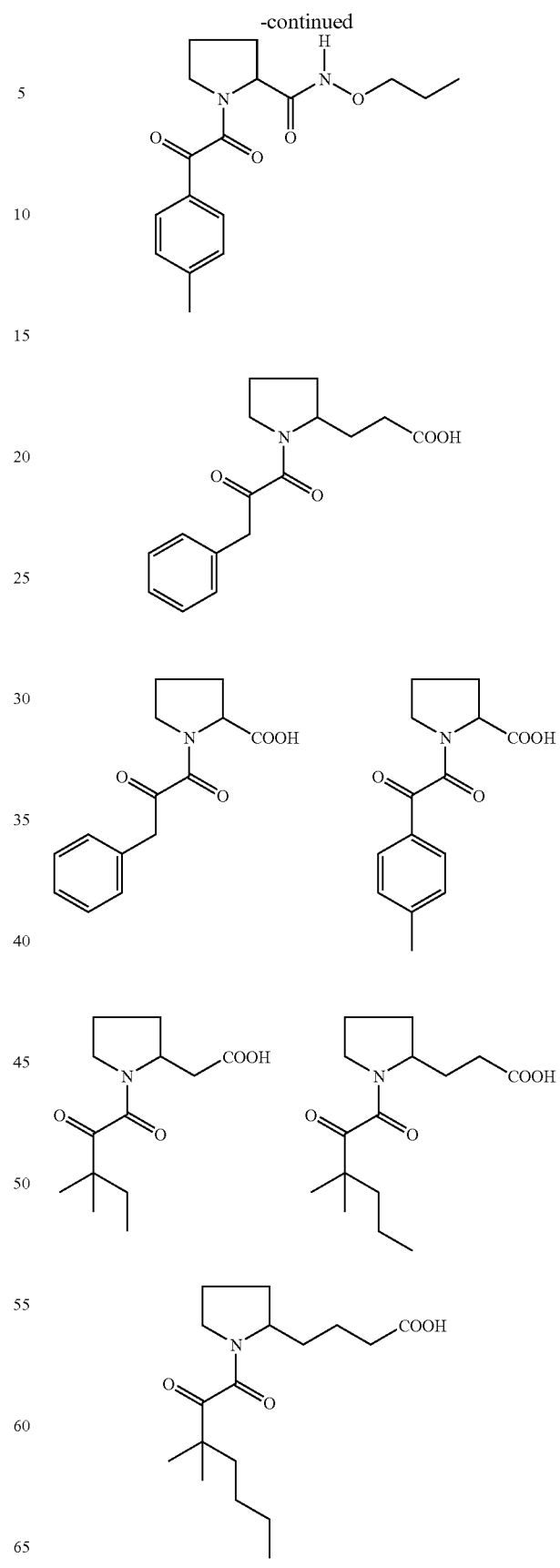

-continued
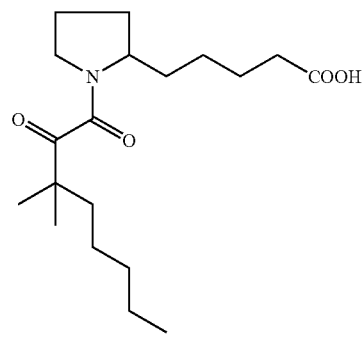
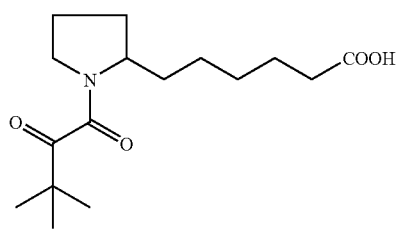
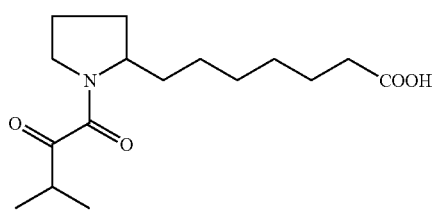
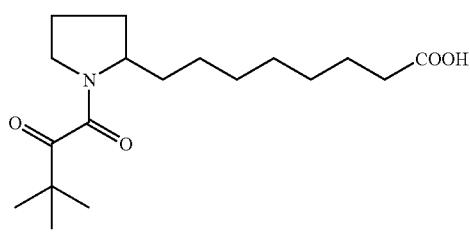
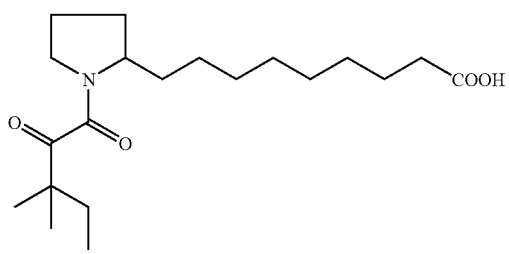
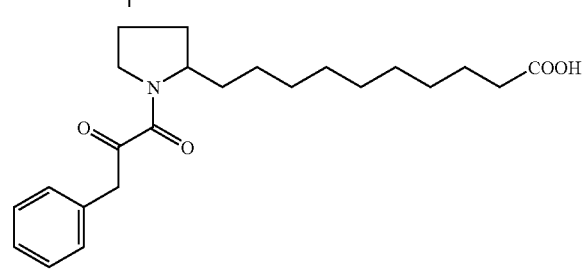
-continued
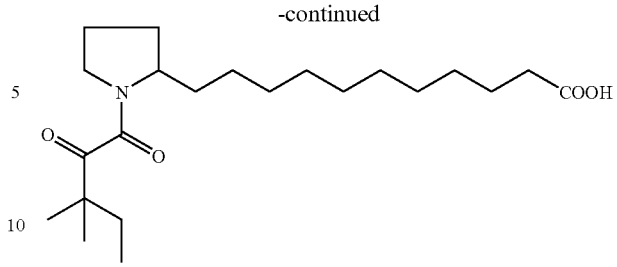
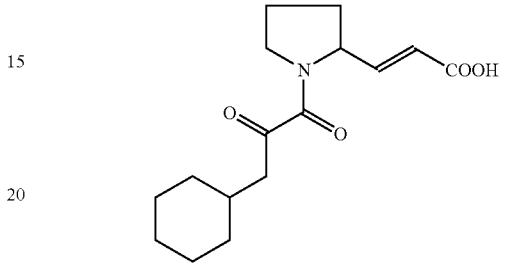
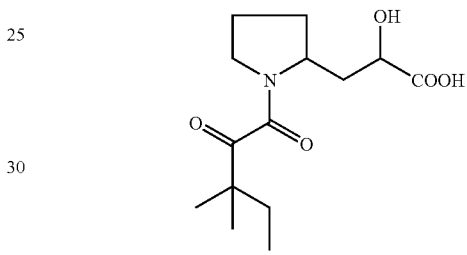
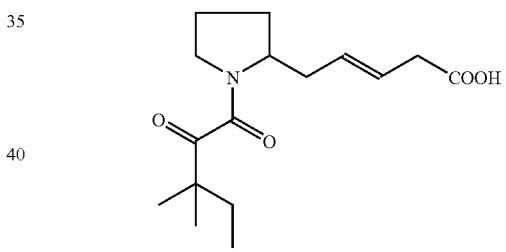
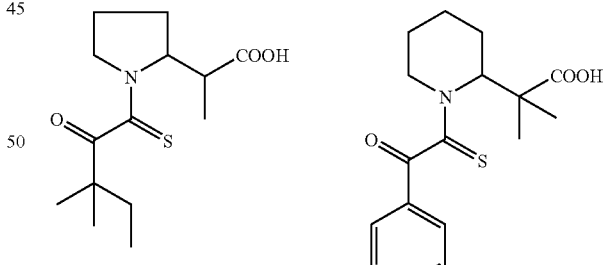
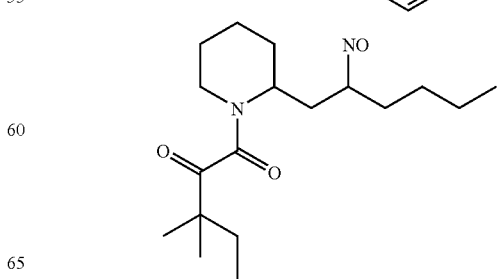

-continued
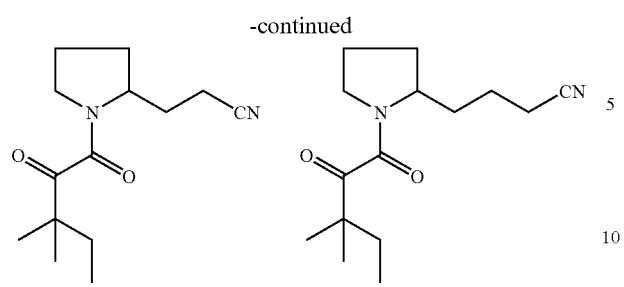
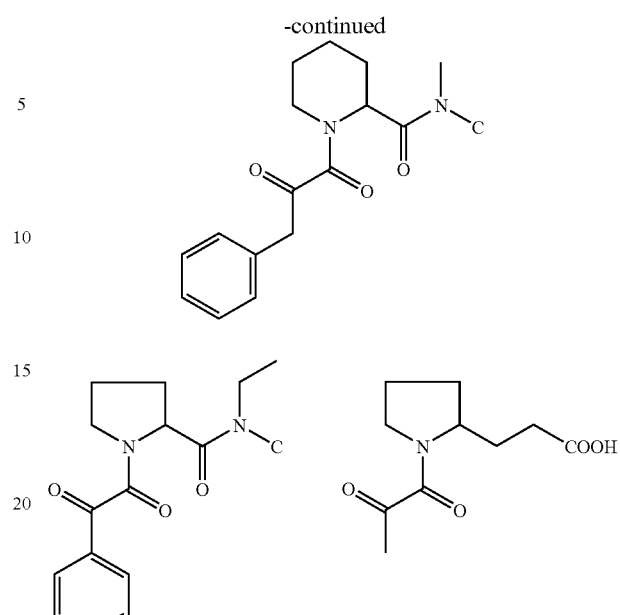
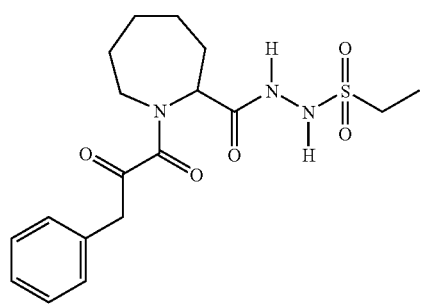
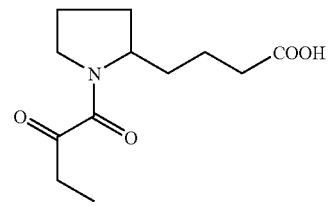
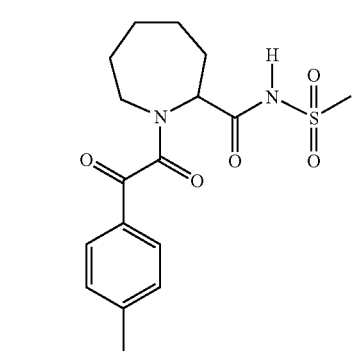
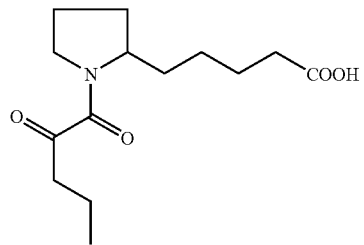
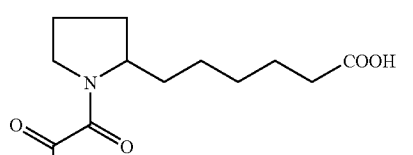
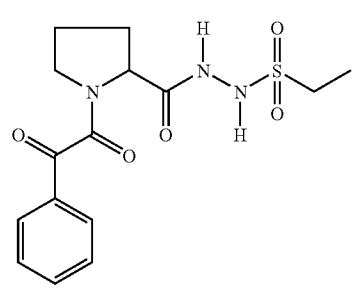
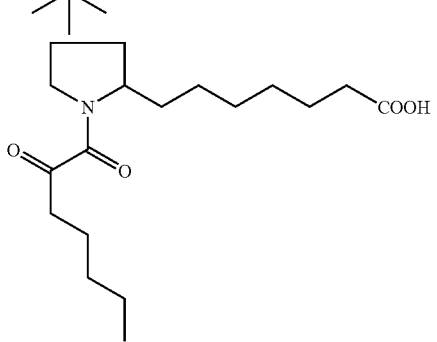

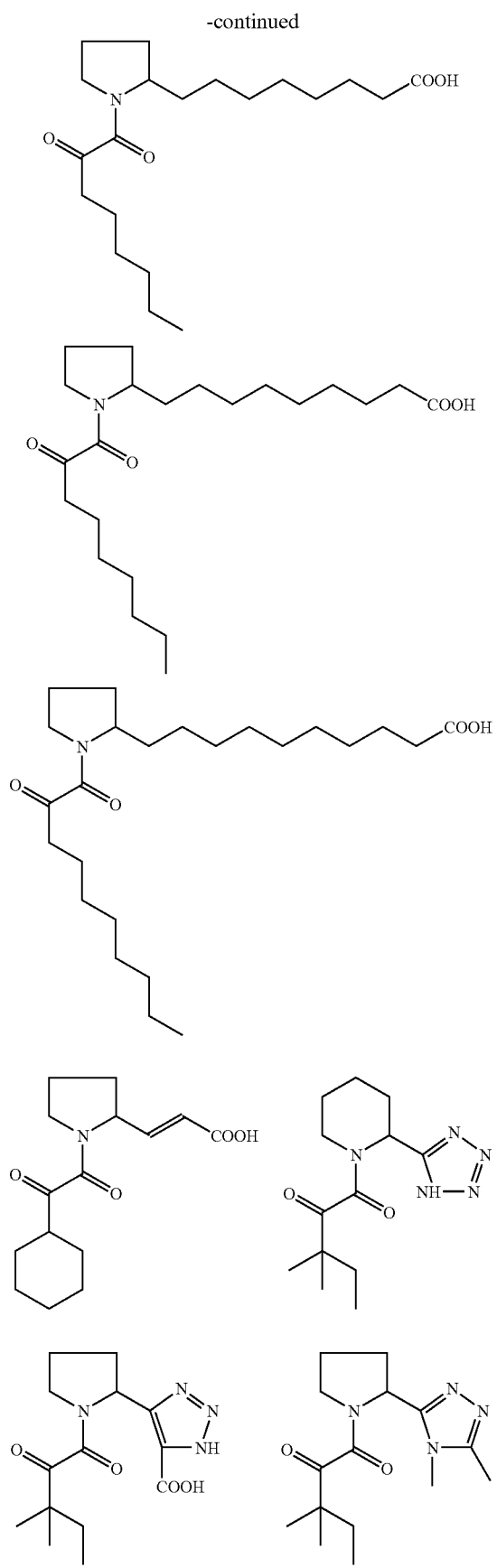

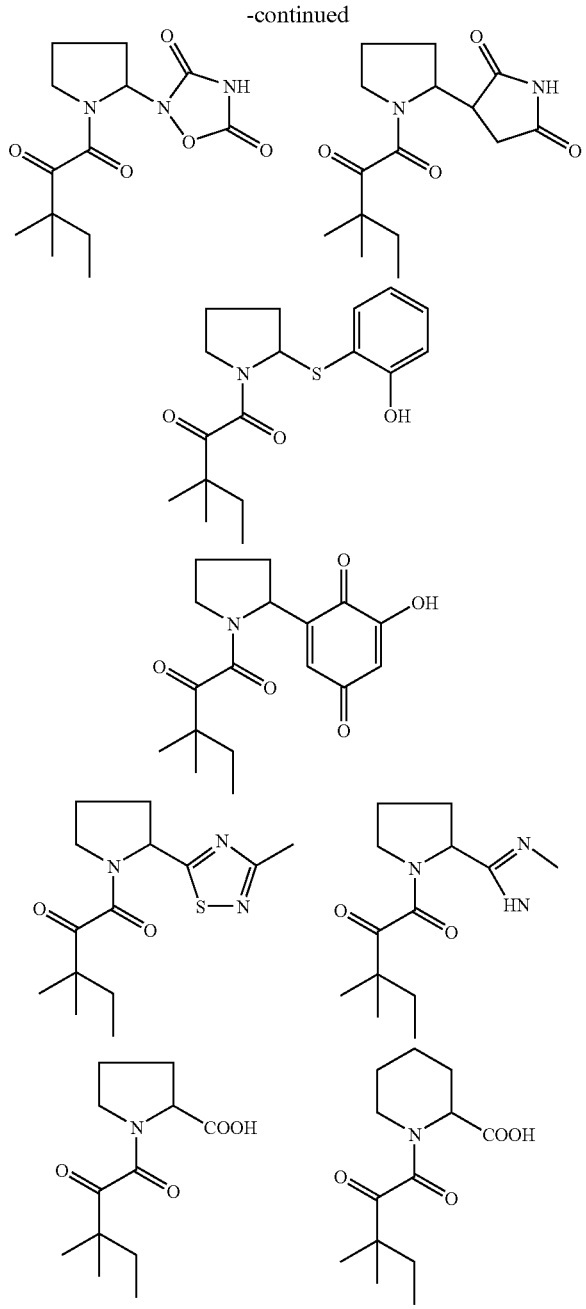

[(2S)-1-(1,2-dioxo-3,3-dimethylpentyl)-2-hydroxymethylpyrrolidine; (2S)-1-(1, 2-dioxo-3,3-dimethylpentyl)-2-pyrrolidinetetrazole; (2S)-1-(1,2-dioxo-3,3-dimethylpentyl)-2-pyrrolidinecarbonitrile; (2S)-1-(1,2-dioxo-3,3-dimethylpentyl)-2-aminocarbonyl piperidine; and compounds 1–25, 27, 28, 31–33, and 35–136 of Tables I, II, and III].

10. The method of claim 1, wherein the compound is non-immunosuppressive.

11. The method of claim 1, wherein the nerve-related vision disorder is retinal ischemia.

12. The method of claim 11, wherein the retinal ischemia is selected from the group consisting of degeneration of retinal ganglion cells, degeneration of optic nerve axons, degeneration of myelin sheaths, ischemic optic neuropathy, and retinal vascular blockage.

13. The method of claim 1, wherein the nerve-related vision disorder is optic nerve transection.

14. The method of claim 13, wherein the optic nerve transection is selected from the group consisting of ganglion cell death after optic nerve transection and myelin degeneration after optic nerve transection.

15. The method of claim 1, wherein the nerve-related vision disorder is diabetes.

16. The method of claim 15, wherein the diabetes is selected from the group consisting of diabetes from degeneration and diabetic retinopathy.

17. The method of claim 1, wherein the nerve-related vision disorder is macular degeneration.

18. The method of claim 1, wherein the nerve-related vision disorder is glaucoma related degeneration.

19. The method of claim 1, wherein the nerve-related vision disorder is cataract related degeneration.

20. The method of claim 1, wherein the nerve-related vision disorder is a detached retina.

21. The method of claim 1, wherein the nerve-related vision disorder is inflammation related degeneration.

22. The method of claim 1, wherein the nerve-related vision disorder is photoreceptor degeneration.

23. The method of claim 1, wherein the nerve-related vision disorder is optic neuritis.

24. The method of claim 1, wherein the nerve-related vision disorder is dry eye degeneration.

25. The method of claim 1, wherein the mammal is human.

* * * * *